United States Patent
Mayo et al.

[11] Patent Number: 6,118,850
[45] Date of Patent: Sep. 12, 2000

[54] ANALYSIS METHODS FOR ENERGY DISPERSIVE X-RAY DIFFRACTION PATTERNS

[75] Inventors: William E. Mayo, Edison, N.J.; Zwi Kalman, Jerusalem, Israel; Mark C. Croft, Highland Park, N.J.; Joseph Wilder, Princeton, N.J.; Richard Mammone, Bridgewater, N.J.; Adam B. Fineberg, Saratoga, Calif.

[73] Assignee: Rutgers, The State University, New Brunswick, N.J.

[21] Appl. No.: 09/451,451

[22] Filed: Nov. 30, 1999

Related U.S. Application Data

[63] Continuation of application No. 09/031,276, Feb. 27, 1998.
[60] Provisional application No. 60/039,062, Feb. 28, 1997.

[51] Int. Cl.$^7$ ...................................................... G01T 1/36
[52] U.S. Cl. .............................................. 378/83; 378/82
[58] Field of Search .................................... 378/4, 82, 83

[56] References Cited

U.S. PATENT DOCUMENTS

| | | | |
|---|---|---|---|
| 5,007,072 | 4/1991 | Jenkins et al. | 88/378 |
| 5,008,911 | 4/1991 | Harding | 378/86 |
| 5,231,652 | 7/1993 | Harding | 378/86 |
| 5,265,144 | 11/1993 | Harding et al. | 378/86 |
| 5,394,453 | 2/1995 | Harding | 278/86 |
| 5,481,476 | 1/1996 | Windig | 364/498 |
| 5,634,087 | 5/1997 | Mammone et al. | 395/24 |

OTHER PUBLICATIONS

Improvement of the Quality of the Data Collected Using a Position–Sensitive Detector, Nuclear Instruments and Methods, vol. 201, (1982), pp. 117–122.

Energy–Dispersive X–Ray Diffraction Tomography, Phys. Med. Biol., vol. 35, No. 1, (1990) pp. 33–41.

Optimization Criteria for CXRS Baggage Inspection, SPIE, vol. 2511, pp. 64–70 (1995).

Scattered X–Ray Beam Nondestructive Testing, Nuclear Instruments and Methods in Physics Research A, vol. 280, (1989) pp. 517–528.

Adaptation of Solid State Detector in X–Ray Powder Diffractometry, X–Ray Spectrometry 1 pp. 8249–8254.(1972).

On The Use of Wide Angle Energy–Sensitive Detectors in White–Beam X–Ray Single Crystal Diffraction, Nuclear Instruments and Methods, vol. 178, (1980), pp. 131–135.

Single and Segmented High Purity Germanium Detectors for Industrial and Medical Applications, Nuclear Techniques for Analytical and Industrial Applications, (1993) pp. 171–174.

Evaluation of High–Pressure X–Ray Diffraction Data from Energy–Dispersive Conical–Slit Equipment, High Temperatures–High Pressures, vol. 16, (1984) pp. 501–505.

Scattered X–Ray Beam Non–Destructive Testing, Nuclear Instruments and Methods in Physics Research A280, (1989) pp. 517–528.

Detection of Explosives in Airport Baggage Using Coherent X–Ray Scatter, SPIE, vol. 2092, Substance Detection Systems, (1993), pp. 399–410.

X–Ray Diffraction: New High–Speed Technique Based on X–Ray Spectrography, Science, vol. 159, No. 2818, Mar. 1, 1968, pp. 973–975.

(List continued on next page.)

*Primary Examiner*—David V. Bruce
*Attorney, Agent, or Firm*—Lerner, David, Littenberg, Krumholz & Mentlik, LLP

[57] ABSTRACT

Energy dispersive x-ray diffraction spectra are obtained from numerous volume elements within an object. A feature set such as a set of cepstrum coefficients is extracted from each spectrum and classified by a trained classifier such as a neural network to provide an indication of whether or not contraband such as explosives is present in the volume element. Indications for adjacent volume elements are evaluated in conjunction with one another, as by an erosion process, to suppress isolated indications and thereby suppress false alarms.

51 Claims, 13 Drawing Sheets

OTHER PUBLICATIONS

Bibliography: The Energy Dispersive X–Ray Diffraction Method: Annotated Bibliography 1968–78, Journal of Materials Science 15 (1980) pp. 269–278.

Status and Outlook of Coherent–X–Ray Scatter Imaging, Optical Society of America, May 1987, vol. 4, No. 5, pp. 933–944.

Superior Court of New Jersey, Appellate Division, Docket No. A–7108–96T5, Defendants–Appellants' Brief, Apr. 30, 1998.

Superior Court of New Jersey, Appellate Division, Docket No. A–7108–96T5, Brief of Plaintiff–Respondent Rutgers, the State University, Jun. 15, 1998.

Superior Court of New Jersey, Law Division: Middlesex County, Docket No. L–113895, Final Order and Judgment, filed Jul. 7, 1997.

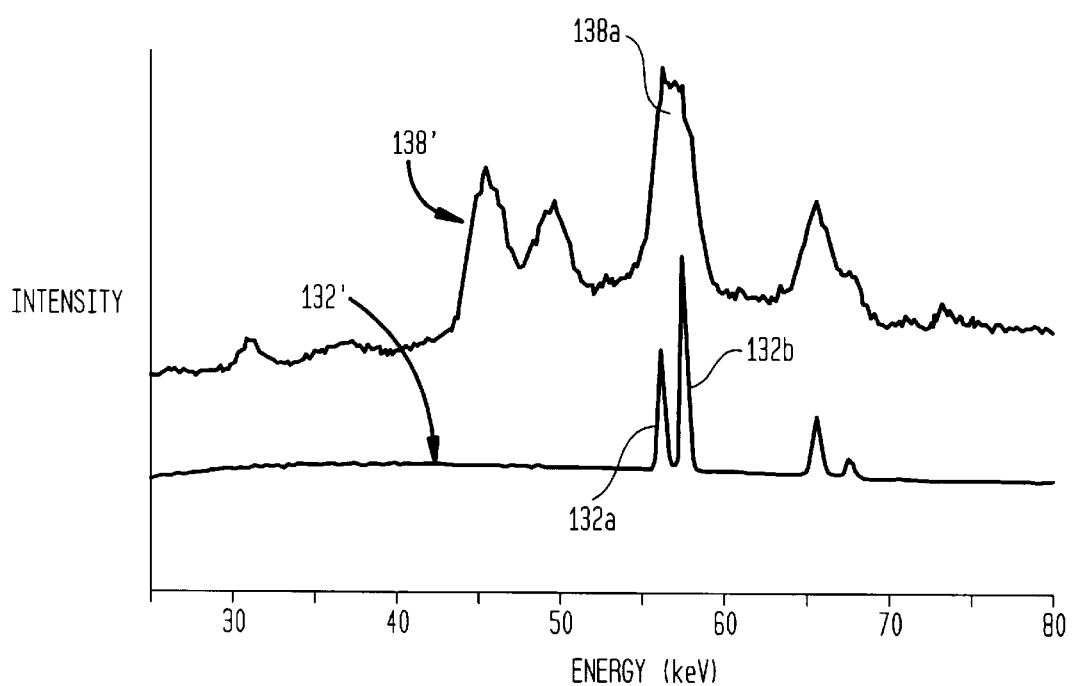

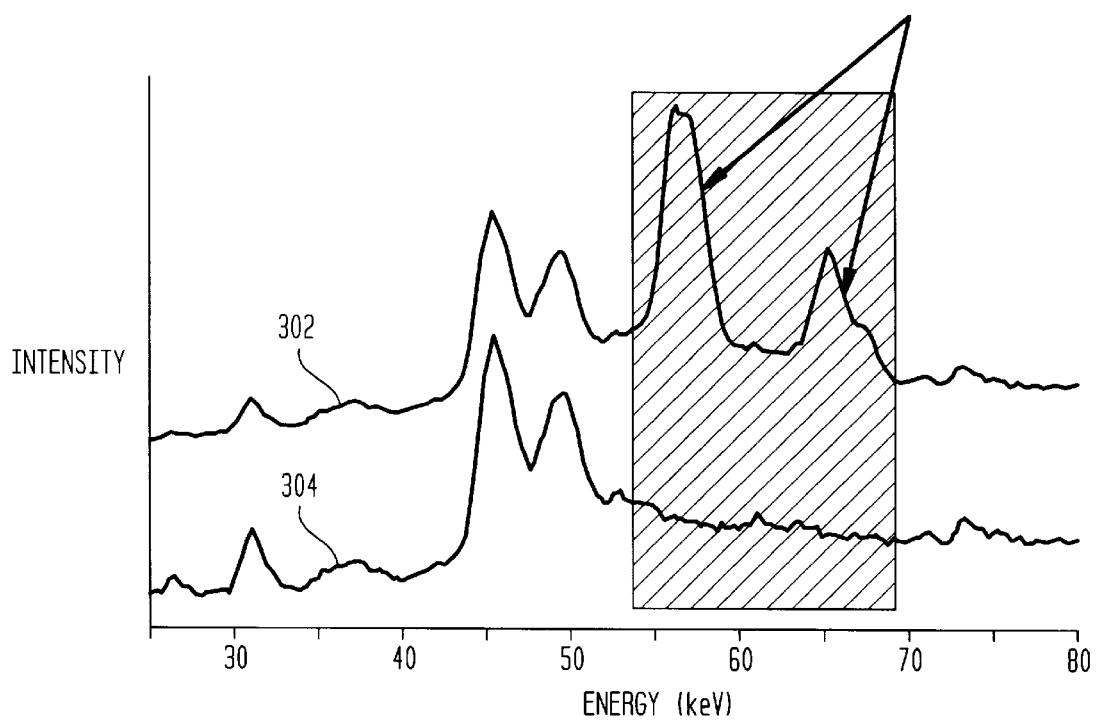

ANALYSIS METHODS FOR ENERGY DISPERSIVE X-RAY DIFFRACTION PATTERNS

CROSS REFERENCE TO RELATED APPLICATIONS

The present application is a continuation of U.S. patent application Ser. No. 09/031,276 filed Feb. 27, 1998, which claims benefit of United States Provisional Patent Application 60/039,062 filed on Feb. 28, 1997, the disclosures of which is incorporated by reference herein. The present application is a continuation of U.S. patent application Ser. No. 09/031,376, filed Feb. 27, 1998.

BACKGROUND OF THE INVENTION

Energy dispersive x-ray (EDXD) diffraction has been used since approximately 1967 to obtain diffraction patterns from crystalline regions within an object. A conventional apparatus for performing EDXD is depicted in FIG. 1. A source 30 generates a polychromatic incident x-ray beam incorporating x-rays of different wavelengths. The incident beam passes through the test object 34 being examined. As the x-ray beam passes through the test object, diffraction occurs. The diffracted x-rays are scattered over a range of angles with respect to the incident beam. A radioopaque plate with a narrow opening 36 is arranged to pass only a relatively narrow beam 38 of diffracted rays along a preselected diffracted beam path. An energy dispersive x-ray detector 40 of known type is arranged to capture the diffracted x-ray beam passing through opening 36. The detector is used to measure the diffracted beam intensity as a function of photon energy, to provide a spectrum of the diffracted x-rays. An example of such a spectrum is illustrated in FIG. 2. A substantial part of the incident beam passes through the test object without diffraction. Some of the undiffracted x-rays are absorbed by the test object. The remainder forms a transmitted beam 42 exiting from the object.

Diffracted beam 38 represents the result of x-ray diffraction in a small volume element at the intersection of incident beam 32 and diffracted beam 38. Spectra can be obtained for other volume elements by moving test object 34 relative to the incident and diffracted beams, i.e., relative to source 30 and opening 36. Also, EDXD can be made tomographic by adding multiple detectors and appropriate beam stops and acceptance slits, so that each detector receives a diffracted beam from a different location along the incident beam. In this mode of operation, each detector "looks" at a single volume element of the three dimensional object. This permits a more rapid inspection of the entire object.

After the diffraction spectrum is obtained, it can be analyzed to determine the crystal structure of the diffracting object. This process consists of determining the positions of the peaks in the diffraction pattern and converting the positions into "d" spacings (through Bragg's law) corresponding to the spacing between parallel planes of the crystalline material. This is the most common application for non-tomographic methods. For example, the apparatus shown in FIG. 1 can be used to measure d spacings of crystalline materials under pressure. The apparatus is equipped with diamond anvils 44 to apply pressure on the test object. These anvils are substantially transparent to the x-rays used in the procedure. Alternatively, the diffraction pattern (assuming it comes from an unknown material) can be compared to a library of standard diffraction patterns in order to identify the material. This is possible because each crystalline material has a unique diffraction pattern—thus, two materials can be distinguished by differences in their diffraction patterns. The focus of the present disclosure will be on the identification of unknown materials, although many of the techniques presented here can also be applied to other EDXD methods where only the "d" spacings and their intensities are desired.

Significant efforts have been devoted in the art to design of EDXD equipment. For example, The design of apparatus suitable for EDXD is set forth in U.S. Pat. Nos. 5,007,072, 5,008,911, 5,231,652 5,265,144 and 5,394,453 in German Published Patent Applications 3682453, 3842146, 4203354, 4222227, 3832146, 3909147, 4019613, 4034602 and 4101544 in European Published Patent Applications 360347, 370347, 462658, and 496454; and in scientific literature including Nucl. Inst. Meth. In Phys. Res. A280 (1989) 517–528, Phys. Med. Biol. 35 (1990) 33–41, SPIE, 2511 (1995) 64–70 and International Conference Proceedings, Nuclear Techniques for Analytical and Industrial Applications, Western Kentucky University 1993, pages 171–174. The disclosures of all of these references are incorporated by reference herein.

Considerable effort has been devoted towards application of EDXD methods using such equipment to identification of unknown materials in a test object. In particular, considerable effort has been devoted heretofore towards development of EDXD methods which can detect contraband substances as explosives and illegal drugs in objects such as parcels and luggage. Practical methods for these applications must meet several demanding conditions. Such a method should be capable of detecting the substances of interest reliably, and should yield only a relatively small number of false indications that a contraband substance is present. The method should be capable of providing such performance despite confounding factors such as variation in the size and x-ray absorptivity of the objects, deliberate attempts to hide the contraband substance by shielding it or by mixing it with other substances. The method also should be usable with real apparatus having imperfections such as x-ray sources with non-uniform emission characteristics. All of these factors taken together pose a significant challenge. Thus, despite all of the efforts in the art heretofore, there has been no truly satisfactory method of EDXD analysis which can be applied in practical detection of contraband substances. There are similar needs for improvement in EDXD methods for other purposes.

SUMMARY OF THE INVENTION

The present invention addresses these needs.

One aspect of the present invention provides a method of examining crystal structures of an object by energy dispersive x-ray diffraction. Methods according to this aspect of the invention include the steps of applying a beam of incident x-ray radiation through the object, detecting diffracted x-ray radiation from the object and deriving a spectrum of the diffracted x-rays. The method according to this aspect of the present invention further includes the step of extracting a plurality of features from the diffracted x-ray spectrum constituting a feature set and classifying the structure of the object by a probabilistic technique in which a plurality of the features in the feature set contribute to the probability that the structure belongs to a particular one of a plurality of classes. For example, the classifying step may include the step of subjecting the features in the feature set to processing in a classifier such as a multilayer perceptron network or a neural tree network which has been trained using one or more spectra representing x-rays diffracted by one or more known substances. Thus, the spectrum as a whole is subjected to a recognition process based on consideration of many features together, rather than an attempt to recognize an individual feature or features of the spectrum as an indication of a particular crystal structure.

The features included in the feature set may include individual elements of the spectrum such as energy and intensity values of peaks or troughs and energy and intensity values of centroids of regions of the spectrum lying within preselected energy ranges. The features may also include parameters of one or more curves, such as regression lines, which are fit to at least some of the aforesaid energy and intensity values. In particularly preferred methods according to this aspect of the present invention, however, the step of extracting the set of features from the spectrum includes the step of applying a transform to the spectrum so as to provide a set of coefficients such that each coefficient depends on the entirety of the spectrum. Such transforms tend to suppress noise in the spectrum. The set of features used in the classifying step desirably includes at least some of the coefficients provided by such a transform. Most preferably, the transform is a cepstrum transform. As further discussed below, the cepstrum transform of the spectrum is the inverse Fourier transform of the logarithm of the absolute value of the Fourier transform of the spectrum. The cepstrum transform tends to de-emphasize variations in peak intensity due to absorption or material variations. Stated another way, the transforms, and particularly the cepstrum transforms provide features which emphasize the real information in the diffraction spectrum. Use of feature sets derived from such transforms in combination with a probabilistic classifying technique results in a particularly effective classification scheme.

Methods according to this aspect of the invention can be used, for example, to provide information representing the likelihood that the object contains a crystal structure, associated with any of several known contraband substances as, for example, any of several known illegal drugs or any of several known explosives. The methods can also provide information representing the likelihood that the object contains a particular one of the known substances, such as a particular explosive or drug. Methods according to this aspect of the present invention can include auxiliary detection steps such as detection of x-ray fluorescence peaks in the spectrum associated with heavy metals mainly found in explosive detonators. Also, the x-ray absorptivity of the object can be monitored; excessive absorptivity indicates that shielding has been used and thus indicates that the presence of contraband is more likely.

Methods according to this aspect of the present invention can be performed separately with respect to each of a plurality of volume elements in the object being examined so as to provide separate structural classification information with respect to each such volume element as, for example, a separate indication of the presence of absence of contraband in that volume element.

A further aspect of the present invention provides additional methods of examining an object. Methods according to this aspect of the invention include the step of obtaining local information with respect to each of a plurality of volume elements in an object and classifying the local information so as to provide a separate indication with respect to each such volume element as to whether a substance of a preselected class is present in that volume element. Methods according to this aspect of the present invention further include the step of evaluating the presence indications obtained with respect to adjacent volume elements in conjunction with one another. This combined evaluation desirably acts to suppress isolated presence indications. For example, presence indications indicating the presence of contraband in a single volume element remote from any other voxel having a similar presence indication can be suppressed. This aspect of the present invention incorporates the realization that in real systems, the substances to be detected rarely are present in only isolated volume elements within the object. Isolated indications that a particular class of structure is present in only one volume element unconnected with any other volume element having the same type of structure present almost always represent spurious data. By ignoring such isolated presence indications the method dramatically reduces the incidence of false indication that a substance such as contraband is present in the object, without materially affecting the ability of the system to detect real contraband or other substances in the object.

In particularly preferred methods according to this aspect of the present invention, the step of evaluating the presence indication for volume elements in conjunction with one another includes processes such as erosion and dilation in which the presence indications in some volume elements are modified depending upon the presence indications in adjacent volume elements. For example, when the presence indication with respect to each volume element is a binary value indicating whether or not a substance of a preselected class is present in the particular volume element, the evaluating step may include the step of testing a given volume element to determine whether a predetermined number of other volume elements within a preselected distance from the given volume element have the same binary indication, and suppressing the binary indication for the given volume element if less than the predetermined number of volume elements within the preselected distance have the same binary indication. This process may be performed using adjacent volume elements in a two dimensional or three dimensional array. Other processes for evaluating presence information in multiple voxels in conjunction with one another can also be used. For example, where the presence information for each volume element includes a probability value, the evaluating step can include steps such as deriving a measure of the correlation between probability values for adjacent volume elements and suppressing poorly correlated presence indications.

The step of obtaining an indication as to whether a substance of a preselected class is present in each volume element may include a wide variety of analytical techniques. In particularly preferred methods, however, both of the aforesaid aspects of the invention are employed. That is, the presence indication for each volume element is derived by applying the methods discussed above involving feature extraction from x-ray diffraction spectra and classification of the resulting features.

Yet another aspect of the present invention provides additional methods for examining an object by energy dispersive x-ray diffraction. A method in accordance with this aspect of the present invention includes the step of applying an incident beam of x-ray radiation to an object and detecting diffracted x-rays from the incident beam which are diffracted by the object over a range of Bragg angles greater than zero, so as to obtain an uncorrected diffraction spectrum. The uncorrected diffraction spectrum will include the true diffraction spectrum of the object convolved with the spectrum of the incident beam, with absorption by the object and with a broadening effect which is caused by the non-zero range of Bragg angles. Thus, the uncorrected diffraction spectrum is affected by the spectrum of the incident beam, i.e., by non-uniform intensity of x-rays at different energies in the incident beam. A peak in the incident beam appearing as a peak in the incident beam spectrum can cause a false peak in the uncorrected diffraction spectrum. Also, unequal absorption of energies at different energies by the object being examined will distort the uncorrected diffraction spectrum. Also as further explained below, a real instrument using an opening of finite size to limit the beam of diffracted x-rays actually collects x-rays along many slightly different beam paths lying at slightly different angles to the incident beam. Individual spectra collected along each of these beam paths have slightly different peak positions. Thus, the peaks of uncorrected spectrum are broader than the peaks which would be expected in a similar spectrum observed using a theoretical instrument in which all of the x-ray photons constituting the diffraction spectrum are collected along exactly the same path.

Methods according to this aspect of the present invention include the step of deriving a raw transmission spectrum which includes the spectrum of the incident beam convolved with the effect of absorption by the object. Most preferably, the raw transmission spectrum is obtained directly by detecting a transmitted beam, i.e., by detecting x-rays from the incident beam which pass through the object undiffracted.

The raw transmission spectrum is subjected to an algorithm which simulates convolution of the raw transmission spectrum with the broadening effect so as to obtain a modified transmission spectrum. Finally, a normalized diffraction spectrum is obtained by dividing the uncorrected diffraction spectrum by the modified transmission spectrum. The modification to the transmission spectrum prior to the dividing step effectively matches the peak widths of the transmission spectrum with those of the diffraction spectrum. This avoids the severe artifacts which can occur if spectra with unmatched peak widths are divided by one another. The algorithm simulating convolution of the raw transmission beam spectrum with the broadening effect may include convolving each data point in the raw transmission spectrum with a Gaussian broadening curve. The method may further include the step of determining an exponent of the Gaussian broadening curve by comparing the breadth of one or more peaks in the uncorrected diffraction spectrum or in another diffraction spectrum taken using the same instrument under substantially the same conditions with at least one peak in a spectrum of the incident beam with a transmitted beam.

In a related method, the reverse procedure is used to match the peak widths of the transmission spectrum to those of the diffraction spectrum. Thus, a modified diffraction spectrum is obtained by subjecting the uncorrected diffraction spectrum to a deconvolution algorithm which is effective to substantially reverse the broadening effect mentioned above. A normalized diffraction spectrum is then obtained by dividing the modified diffraction spectrum by the raw transmission spectrum.

The normalized diffraction spectra provided by methods in accordance with these aspects of the invention can be used in the aforementioned methods. Thus, the normalized diffraction spectrum can be subjected to the feature extraction and other steps mentioned above.

These and other objects, features and advantages of the present invention will be more readily apparent from the detailed description of the preferred embodiments set forth below, taken in conjunction with the accompanying drawings.

BRIEF DESCRIPTION OF THE DRAWINGS

FIG. 3 is a graph of a further uncorrected diffraction spectrum in conjunction with an unmodified transmitted beam spectrum.

FIG. 5 is a graph depicting a spectrum before and after normalization processing.

FIG. 14 is a graph showing FIG. 13 but showing the same data after evaluation of plural volume elements in conjunction with one another.

Figure 8:
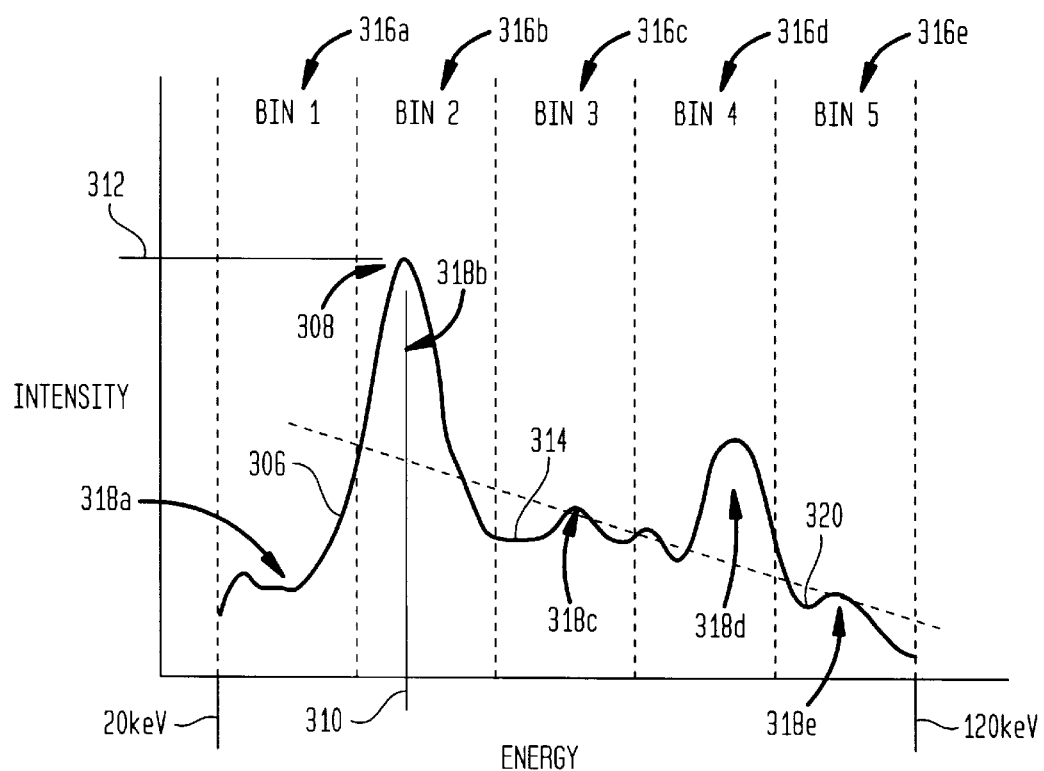
FIG. 8 is a schematic diagram depicting a diffraction spectrum in conjunction with certain features extracted from such spectrum.
Figure 15:
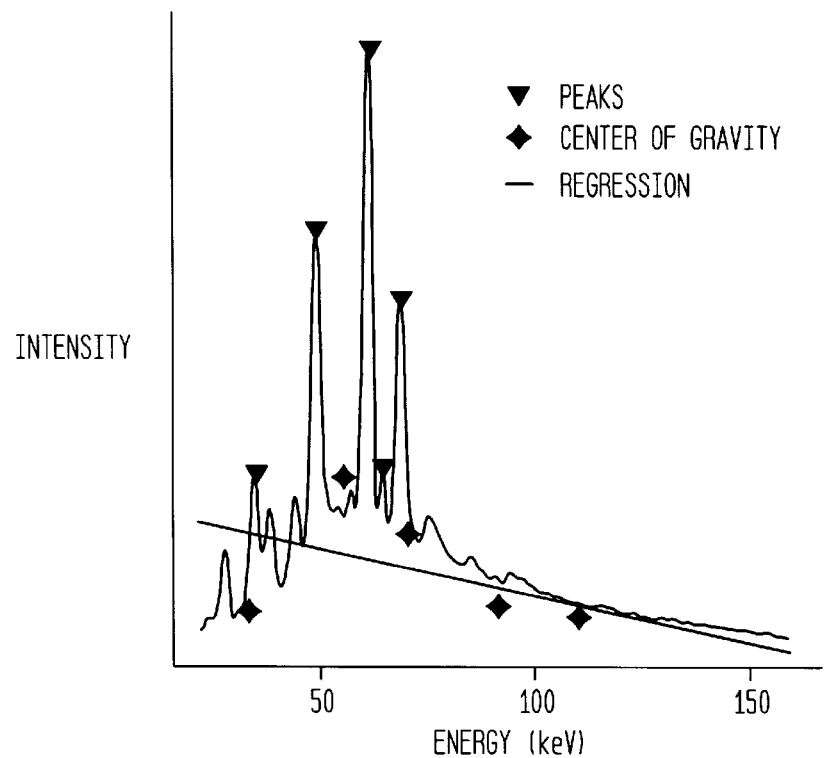
Figure 16:
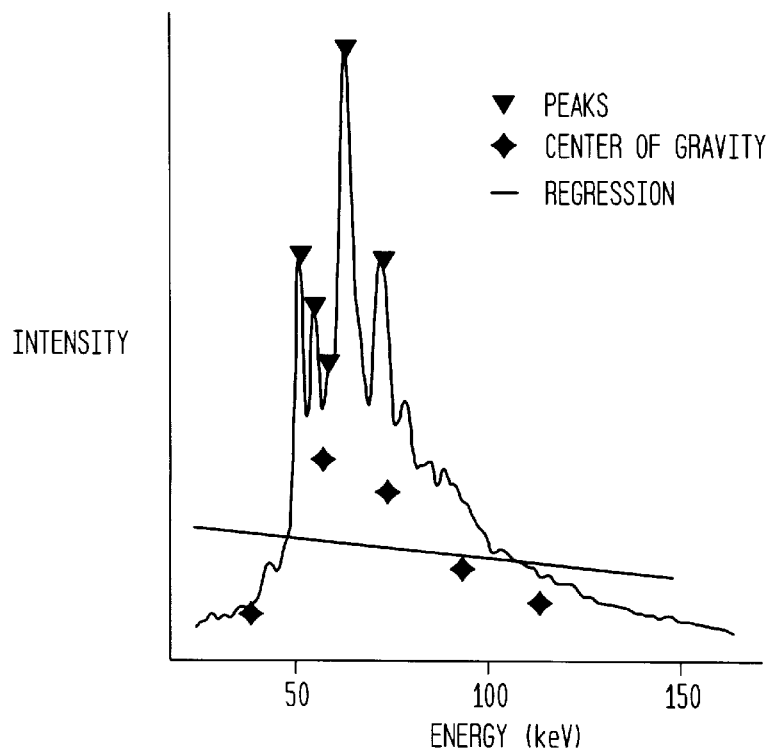

Each of FIGS. 15 and 16 is a view similar to FIG. 8, but depicting spectra and features derived from examination of different materials.

Figure 17:
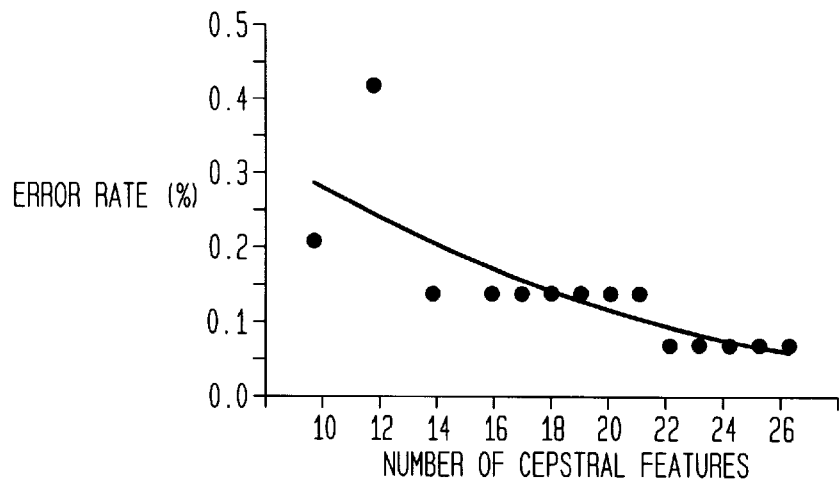

FIG. 17 is a plot of error rate in a set of methods according to further embodiments of the invention.

Figure 18A:
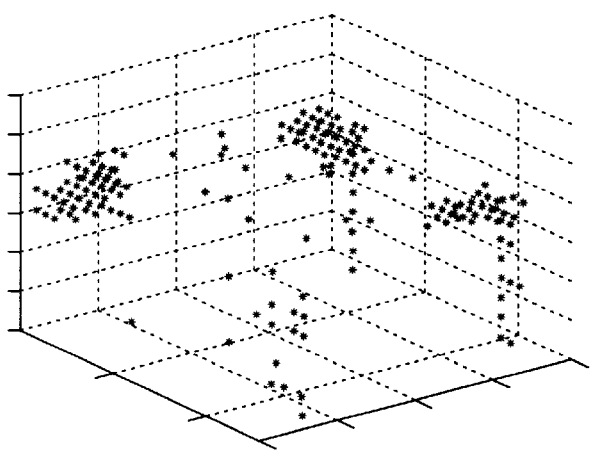

FIG. 18A is a three-dimensional graph depicting binary presence data obtained in one exemplary process during an intermediate stage of the process.

Figure 18B:
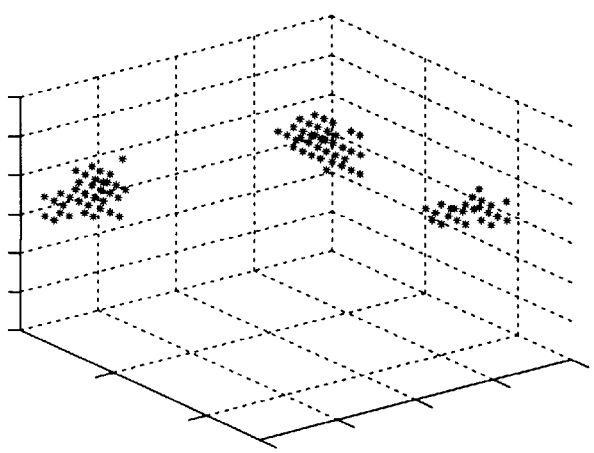

FIG. 18B is a graph similar to FIG. 18A depicting the same binary presence data at a later stage in the process, after evaluation of presence indications for individual voxels in conjunction with presence indications for adjacent voxels.

Figure 19:
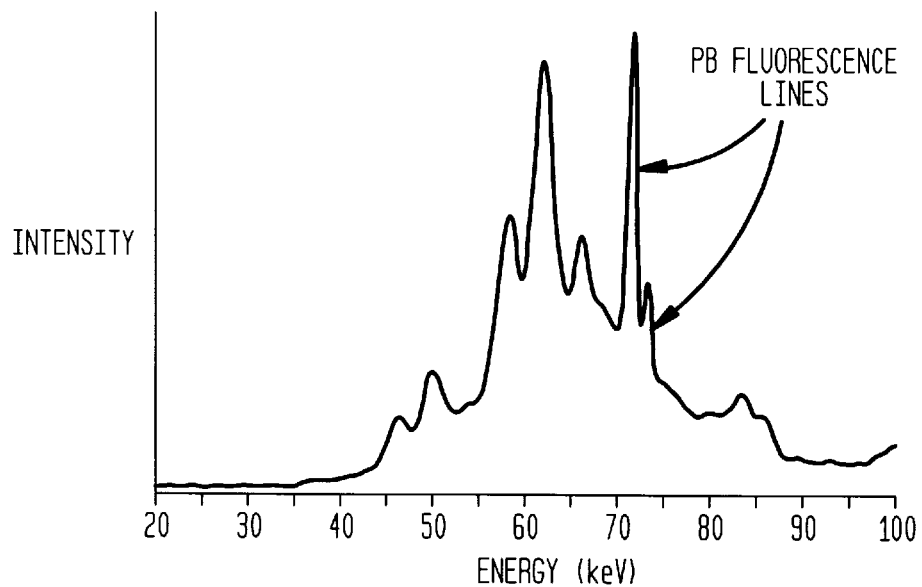

FIG. 19 is a graph depicting a further spectrum.

Figure 20:
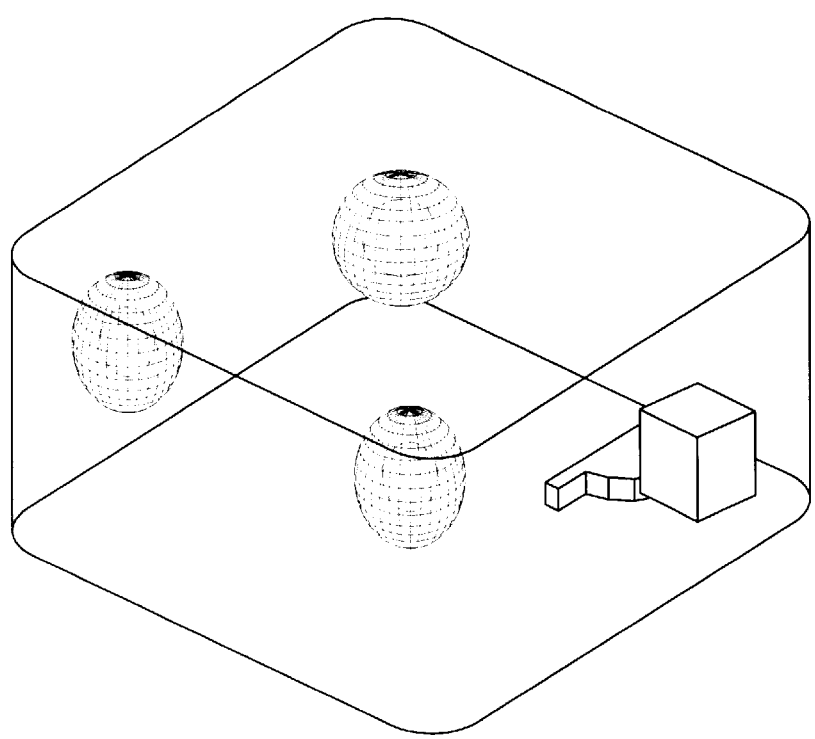

FIG. 20 is a computer generated diagram depicting an object in conjunction with explosives and an absorber located in a method according to a further example of the invention.

DETAILED DESCRIPTION OF THE PREFERRED EMBODIMENTS

The methods discussed below determine the presence of target crystalline objects within a larger object (crystalline or noncrystalline) that may obscure the target. The examples presented here illustrate identification of explosives, but any crystalline material can be detected in a similar way. The preferred methods include the following steps:

preprocessing—the diffraction spectra are modified to correct for system dependent artifacts such as source characteristic lines, absorption edges, variation in diffraction angle, noise reduction, and so forth.

feature extraction—the modified diffraction spectrum is examined and the key information is extracted that will allow an unique identification of the pattern.

classification—the extracted features are classified by one of a variety of methods to compare the pattern with a library of standard patterns in order to identify the material being examined.

post-processing—after the classifier has determined the identity of the target material, a post-processing procedure is implemented to increase the reliability of the identification and reduce the number of false identifications.

X-RAY BEAM APPLICATION

In a method according to one embodiment of the invention, x-ray diffraction data is obtained using apparatus designed in accordance with known principles as set forth in the references mentioned above. This apparatus was designed to operate with a tungsten x-ray source operating at 160 keV which generated an approximate point source of x-rays. These x-rays were passed through a tubular collimator of approximately 0.1 mm inner diameter to further collimate the incident beam. The distance between the x-ray source and the target object was less than 20 cm, while the target object to detector distance was approximately 2 m, with the detector held at an angular position θ of approximately 3.25° (0.057 rad). Thus, an X-ray source 130 (FIG. 4A) applies an incident beam of x-ray radiation 132 to the object 134 being examined. The major portion of the incident beam is not diffracted, but instead is transmitted through the object, with some absorption by the materials in the object. The portion remaining after absorption exits from the object as a transmitted beam 142 coaxial with the incident beam. An energy-dispersive reference detector 146 is provided in alignment with the path of the transmitted beam. A radioopaque shield with a small pinhole slit 148 passes only a small portion of the transmitted beam to reference detector 146. Portions of the incident beam are diffracted by materials in object 134. An opening or slit 136 accepts a narrow diffracted beam 138 of x-rays directed at a diffraction angle or Bragg angle θ from a small volume element within object 134 and passes the diffracted beam to a further energy-dispersive detector 140. Detectors 140 is operated in the conventional manner to provide an uncorrected energy-dispersive spectrum or plot of intensity versus energy of the diffracted beam 138, whereas reference detector 146 is operated to capture an uncorrected or "raw" energy dispersive spectrum of the transmitted beam. The diffraction angle θ is exaggerated in FIG. 4A for clarity of illustration. In actual practice, the diffraction angle preferably is less than about 3.6 degrees, and more preferably less than about 2.9 degrees. Thus, the transmitted beam and the diffracted beam pass through almost the same thickness of object 134, and pass through almost the same portions of the object. Accordingly, the effect of absorption in the object is almost identical for both the transmitted and diffracted beams. An equivalent embodiment of this design is one which utilizes only a single detector that is alternatively placed on a rotating stage to permit it to act as both detector 140 and 146.

Figure 1:
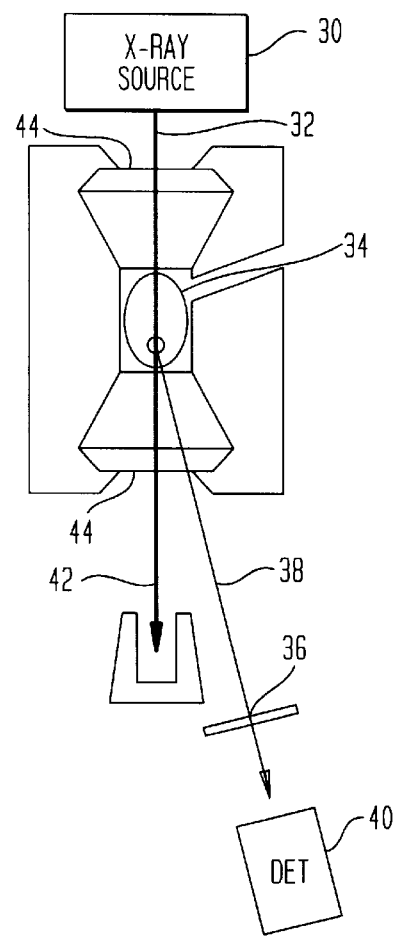
FIG. 1 is a schematic view of conventional EDXD apparatus.
Figure 2:
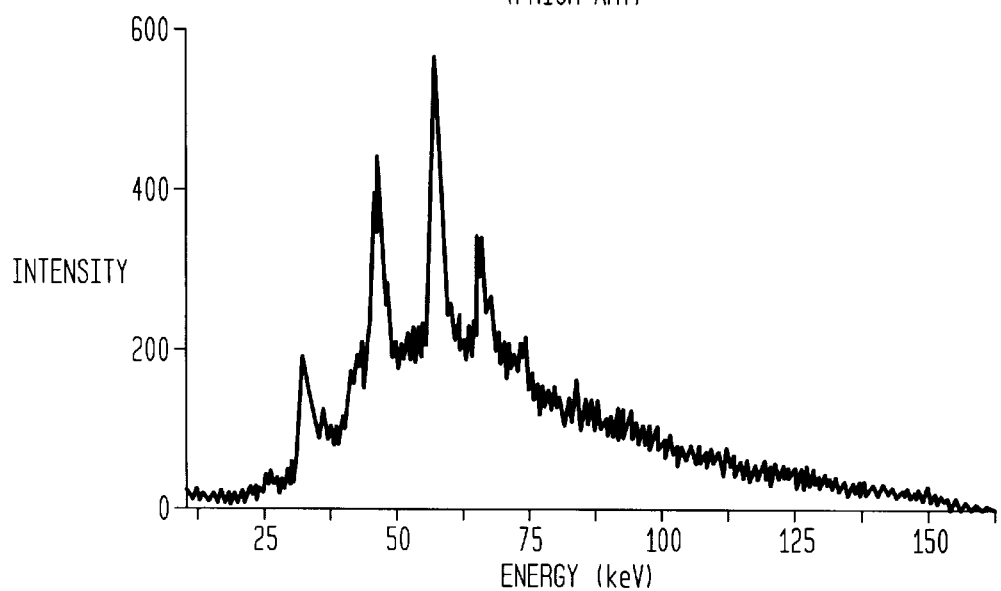
FIG. 2 is a diffraction spectrum of explosive TNT.
Figure 4A:
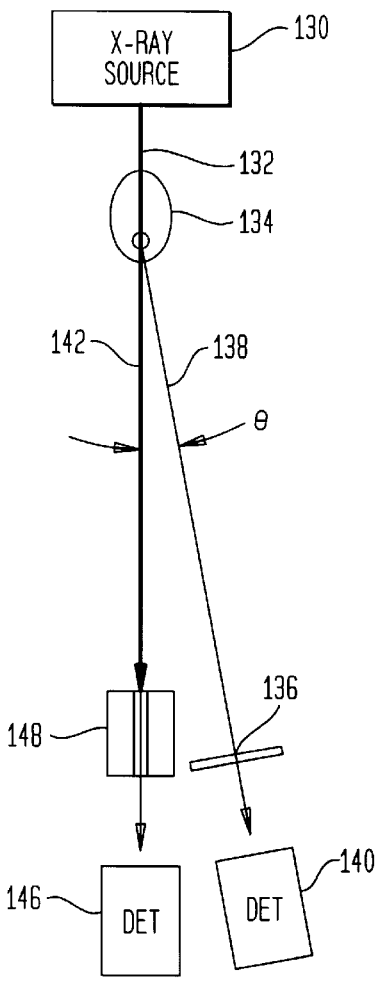
FIG. 4A is a view similar to FIG. 1, but depicting apparatus usable in methods according to one embodiment of the invention.

The particular apparatus illustrated in FIG. 4A is a simple apparatus which acquires only a single diffracted beam from a single volume element within the object at one time. As is well known in the art, certain EDXD instruments acquire a plurality of diffracted beams from a plurality of volume elements. For example, certain known EDXD instruments provide an incident beam in the form of a hollow cone 232, and provide an array of annular detectors 240 coaxial with the axis 231 conical incident beam. The detectors are equipped with beam limiting devices or slits 236 so that each detector 240 receives a converging conical diffracted beam 238 from an annular volume element 235 corresponding to an intersection of the converging and diverging cones. The various annular volume elements may be disposed at different locations along the axis of the conical incident beam, so that when object 234 is moved in a plane transverse to the axis 231 of the beams, various circular volume elements sweep through slices of object 234 in different planes transverse to the axis. Here again, a reference energy-dispersive detector (not shown) is provided for capturing a portion of the transmitted beam which passes through the object without diffraction.

Conical beam arrangements of this type are shown, for example, in U.S. Pat. No. 5,394,453. Unless otherwise specified, experimental data set forth in the present specification refers to experiments using a beam configuration of this type, with 12 annular detectors receiving beams from 12 separate circular volume elements, and with a rotating anode x-ray generator operating in the 160 keV range. This structure also has a central detector of 0 Bragg angle for detecting the transmitted beam. The detectors in such apparatus may be formed from intrinsic germanium, i.e., germanium without p-type or n-type dopants, and are cryogenically cooled. The device constructed for collection of the energy dispersive diffraction patterns was designed according to the design principles disclosed in the U.S. Pat. No. 5,394,453. The major design elements are shown in FIG. 3 of that patent. Specifically, the x-ray source operated at 160 keV with a tungsten anode; the incident beam slit had an angular opening of approximately 2.3° to produce a spot size of 55 mm at the top of the object space; an object space of approximately 600 mm opening; four receiving slits that defined the diffraction angles ranging from approximately 2.9° to 3.4°; and a segmented Ge detector of 80 mm outer diameter with thirteen segmented annular rings designed according to equations 1 and 2 of that patent. The geometry of the slit openings, spacings and distances are based upon these basic design element criteria and the details on generating the component dimensions are described in the preferred embodiment of 5,394,453, which is incorporated by reference herein.

The foregoing details of the apparatus provided solely for ease of understanding. The present methods are equally applicable to any type of beam configuration, and to EDXD spectra obtained with any type of detector. Accordingly, the method steps are described below with reference to the simple apparatus of FIG. 4A for ease of understanding.

PREPROCESSING

The uncorrected spectrum or diffraction pattern captured by detector 140 includes artifacts arising from the instrument and from other sources. The purpose of the preprocessing steps is to remove as many of these as possible so that the resulting pattern is machine independent, and represents the true diffraction spectrum of the material in the object.

The diffracted x-ray signal will contain several artifacts that originate with the incident beam. Of particular importance are the emission or characteristic peak(s) and absorption edges in the incident beam spectrum that result from the choice of x-ray tube target material. The most common material used as an x-ray tube target is tungsten (W). The strongest characteristic peaks for W occur at 59.3 and 57.8 keV, with less intense peaks at 67.0, 67.3, 69.0, and 69.1 keV. Also, a small absorption edge occurs at 69.6 keV. Thus, the incident x-ray beam 132 contains a number of distinctive features that will complicate the analysis of the diffracted beam since these features will be carried through to the diffracted beam. This effect is shown in FIG. 3 where the spectrum 132' of the incident beam and the spectrum 138' diffracted beams are shown.

Figure 7:
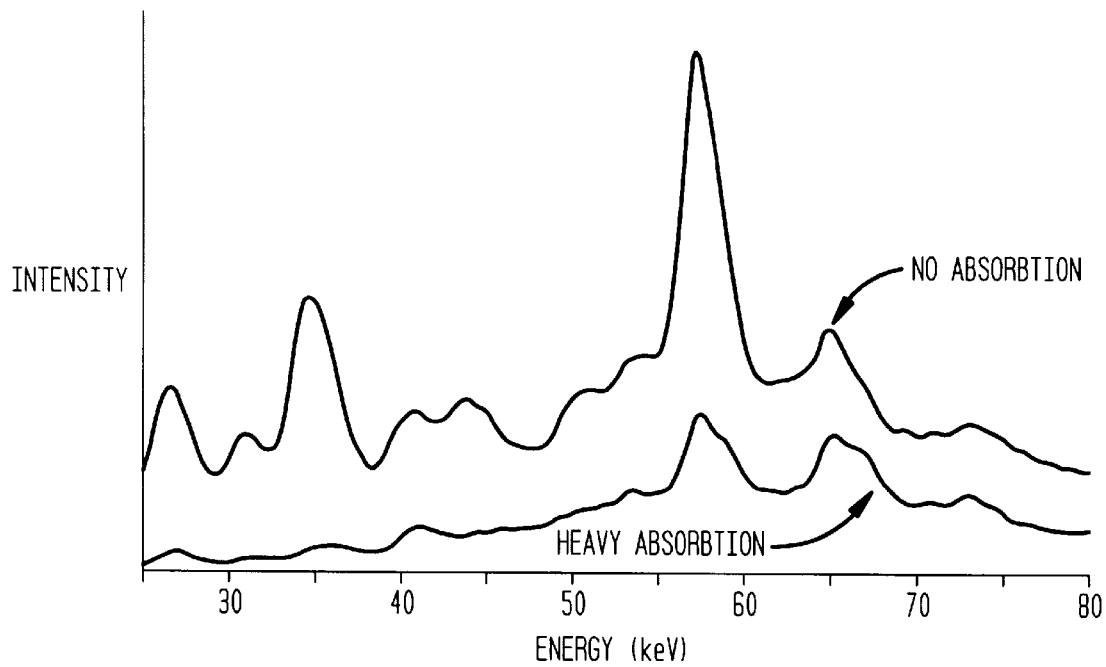
FIG. 7 is a graph of diffraction spectra of C4 explosive with and without a heavy absorber.

Also, as the incident and diffracted x-ray beams pass through the test object and the material surrounding it, non-uniform absorption will take place. The lowest energy portion of the spectra will be preferentially absorbed while the highest energy portion passes through with little loss of intensity. This is shown in FIG. 7 where the spectrum for C-4 plastic explosive with and without heavy absorbers on either side of the test material. Note that the diffraction peaks at 66, 67, and 74 keV suffer almost no absorption while the peak at 57 keV suffers moderate absorption and peaks below 50 keV suffer almost total absorption.

In the preprocessing step, these artifacts are removed from the uncorrected diffraction spectrum using the raw transmission spectrum collected by reference detector 146. The raw transmission spectrum includes the spectrum of the incident beam 132 convolved with absorption by object 134 and the instrumental broadening. Because the transmitted beam 142 and diffracted beam 138 take slightly different paths through object 134, the absorption incorporated in the raw transmitted beam spectrum differs slightly from the absorption incorporated in the uncorrected diffraction spectrum. However, for small diffraction angles θ the path lengths for both the incident and diffracted beams is almost identical as can be readily seen in FIG. 4A. Where the diffraction angle is approximately 3.0 degrees or less, the diffracted beam path length is only 0.1% longer than the direct or transmitted beam path length. Both beams pass through the same material and suffer essentially the same degree of absorption. For example, both beams suffer large absorption at low energies and almost no absorption at the higher energies. Thus, the raw transmission spectrum captured by reference detector 146 can be taken as representing the incident beam spectrum modified by the same absorption which affects the uncorrected diffraction spectrum obtained by detector 140. At first glance, it would appear that the effects of incident beam spectrum and absorption can be removed from the uncorrected beam spectrum simply by dividing the uncorrected beam spectrum by the raw transmission spectrum.

However, the spectral lines in the uncorrected diffraction spectrum are much broader than the same lines in the incident beam or transmitted beam. This effect is seen in FIG. 3. For example, the broad peak 138a in the uncorrected diffraction spectrum arises from two narrow peaks 132a and 132b in the incident beam spectrum. The peak-broadening effect is due to the fact that the diffracted beam is generated by a finite volume rather than from a theoretical point. Stated another way, because slit 136 is of non-zero size, the diffracted beam 138 includes x-rays diffracted over a small but non-zero range of Bragg angles (approximately 0.2°, in typical systems). As further explained below, the location of each peak in an energy-dispersive diffraction spectrum varies with the diffraction angle at which the spectrum is acquired. Because the uncorrected diffraction spectrum acquired by detector 140 represents a composite of spectra acquired at various Bragg angles, each peak is distributed over a continuum of locations. This effect does not occur in the incident beam 132 or in the transmitted beam 142, and thus does not appear in the raw transmitted beam spectrum.

As will be apparent from inspection of FIG. 3, any attempt to use simple division to normalize an uncorrected diffraction spectrum by a spectrum with narrower peaks would result in introduction of high frequency ripples. For example, if spectrum 138' were simply divided by spectrum 132', a new spurious peak would appear at an energy between the energies of peaks 132a and 132b. Thus, before any normalization is attempted, the raw transmission spectrum obtained by the reference detector is mathematically broadened over an energy range comparable to the broadening effect induced in the uncorrected diffraction spectrum by the spread in Bragg angles.

This can be done via a mathematical procedure known as convolution of the incident beam spectra with a Gaussian shaped curve whose halfwidth β is determined directly from experiment. The Gaussian curve is a mathematical function such as $$f(x) = e^{\frac{-x^2}{7.53\beta^2}} \tag{1}$$

where X represents the photon energy.

This Gaussian curve is used in the convolution of the raw transmission spectrum to produce broader peaks typical of the diffracted peaks. An estimate of the halfwidth to be used is obtained by experimental measurement of one or more corresponding peaks in the incident or transmitted beams, and the corresponding peak or peaks in the diffracted beam. As an example, the diffracted peak at 57 keV in FIG. 3 has a halfwidth $\beta_d$ (full width at half maximum) of approximately 1.8 keV (or 3.15%). By comparison, the halfwidth of the characteristic lines in the incident beam $\beta_o$ is only 0.36 keV (or 0.6%), which is close to the intrinsic energy resolution of the detector material operating at cryogenic temperature. From these two measurements, the contribution $\beta_m$ of the machine to the broadening can be estimated by $$\beta_d^2 = \beta_o^2 + \beta_m^2 \tag{2}$$

Thus, in this present example, $\beta_o=0.006$ and $\beta_d=0.0315$, from which one obtains $\beta_m=0.0309$. This value is then used to construct the Gaussian curve of equation 1, which is then convolved with the raw transmission spectrum to provide a modified transmission spectrum. The modification process also compensates for other differences in peak broadening between the raw transmission spectrum and the uncorrected diffraction spectrum, such as those caused by the characteristics of the detectors and pinhole. Finally, the normalization is performed by dividing the uncorrected diffraction spectrum by the modified transmission spectrum. Where plural detectors are employed to obtain a plurality of uncorrected diffraction spectra, each such uncorrected spectrum is normalized in the same manner.

If done correctly, normalization of the uncorrected diffraction spectrum by the modified transmission spectrum removes the unwanted peaks with few artifacts. For example, FIG. 5 shows an uncorrected diffraction spectrum 302 for the explosive PETN together with the normalized spectrum 304 derived from spectrum 302. One consequence of the normalization process, however, is an increase in the noise level due to division of one noisy signal by another noisy signal as seen in normalized spectrum 304. This random noise can be removed by standard noise reduction processes such as smoothing or filtering. Moreover, the preferred feature extraction techniques set forth below substantially suppress the effects of high-frequency noise in the signal.

In the procedure discussed above, the raw transmission spectrum is obtained directly by reference detector 146. However, an equivalent raw transmission spectrum can be obtained indirectly, as by measuring the absorption of the object separately, detecting the spectrum of the incident beam before absorption and mathematically convolving the incident beam spectrum with the absorption of the test object. In this variant, the broadening function can be applied to both the incident beam spectrum and the absorption spectrum before combining the incident beam spectrum with the absorption spectrum, or else can be applied to the raw transmission spectrum resulting from the combining step. Also, the step of dividing the uncorrected diffraction spectrum by the raw transmitted beam spectrum can be performed piecemeal, as by dividing the uncorrected diffraction spectrum first by the broadened incident beam spectrum and then by the broadened absorption function.

Most preferably, a new raw transmission spectrum is acquired each time a diffraction pattern is taken, and the transmission spectrum is acquired simultaneously with the diffraction spectrum. This avoids variations due to changes in operating conditions of the x-ray source and the detectors. However, where the x-ray source and detectors operate under particularly stable conditions, a stored raw transmission spectrum can be used. Alternatively, a stored incident beam spectrum can be combined with a newly-measured absorption spectrum of the object to yield a new raw transmission spectrum.

In a variant of the normalization procedure, the broadening function used to modify the transmission spectrum can be calculated from the parameters of the instrument, rather than determined by experiment. This spread in diffraction angles is dictated by the design of the collimator slits and is under the control of the designer. Thus, the amount of broadening in the uncorrected diffraction spectrum, and hence the amount of broadening which must be applied to the raw transmission spectrum, are predictable in advance based upon knowledge of the system design, the detector material characteristics, and the interplay between the diffracted peak broadening and the geometrical parameters such as slit sizes, path lengths, diffraction angles and so forth. Known techniques such as ray tracing and computer simulation of the diffraction process can be employed in predicting the broadening function.

In a further variant of the normalization process, the techniques used to predict broadening are applied to develop the reverse or deconvolution function which, when applied to the uncorrected diffraction spectrum, will substantially reverse the effect of broadening due to the range of diffraction angles. This deconvolution function is then applied to the uncorrected diffraction spectrum to yield a modified diffraction spectrum. The modified diffraction spectrum is then divided by the raw transmission spectrum. The net effect—matching the peak widths before division—is similar to the processes discussed above.

An alternate procedure to correct for the incident beam artifacts is to use a simple masking procedure on the diffracted spectrum. In this procedure, the position of any tungsten characteristic lines is known and this information is used to blank out that region in the diffracted spectrum. Thus, any diffraction peaks that occur in the 54–61 and the 63 to 69 keV regions are simply ignored since this is the range where the artifacts will occur. The problem with this procedure is that not all the artifacts such as the absorption edge are removed. Moreover, this procedure does not compensate for absorption effects. Thus, the normalization process described above is the preferred method.

Figure 6A:
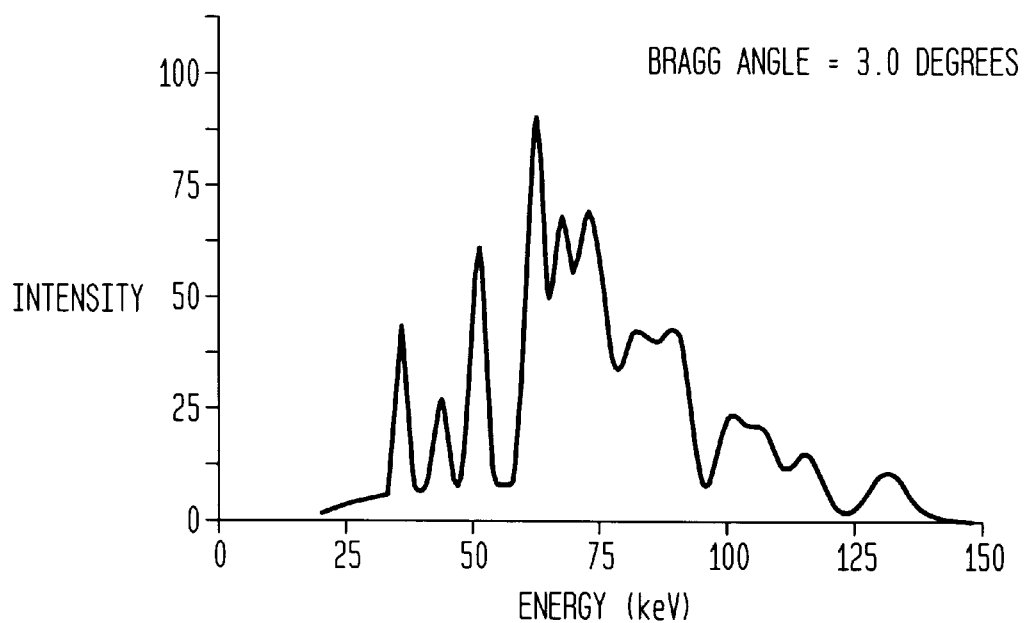
FIGS. 6A and 6B are graphs depicting diffraction spectra of the same substance captured at two slightly different Bragg angles.
Figure 6B:
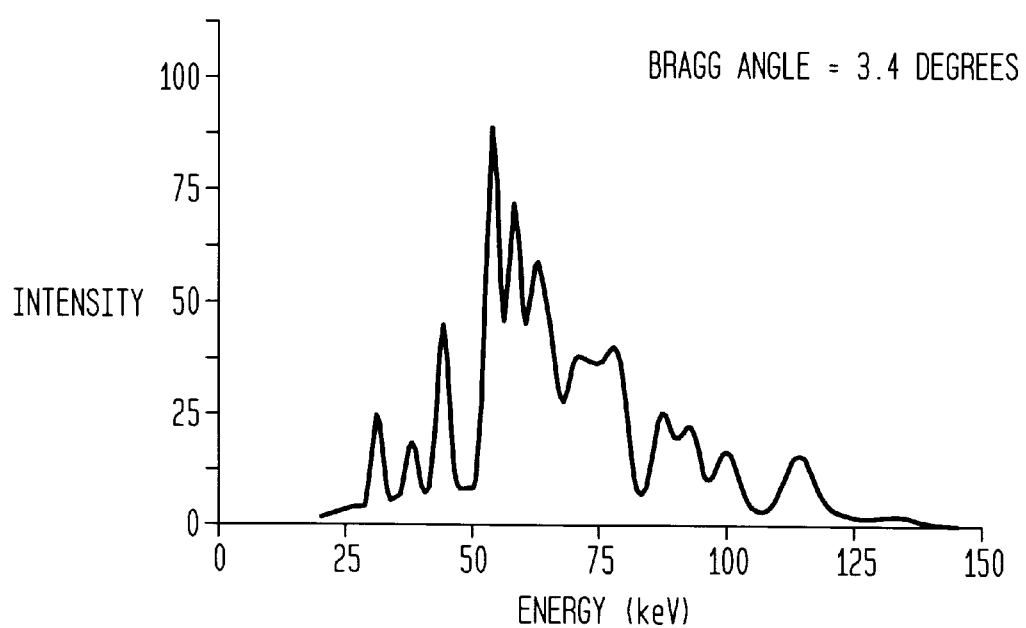

The diffraction angle or Bragg angle θ employed also influences the diffraction spectrum. FIG. 6A depicts a calculated EDXD patterns for PETN explosive acquired by a detector placed at an angle of 3.0 degrees with respect to the incident beam direction (Bragg angle), whereas FIG. 6B shows the corresponding pattern calculated for a detector at a Bragg angle of 3.4 degrees In FIG. 6B, the peaks are shifted to lower energy levels. In a single detector system (like that shown in FIG. 4A), this compression of the diffraction pattern with diffraction angle is not important. However, in a multidetector system (like that shown in FIG. 4B) or the more complex tomographic systems, each detector will likely be at a slightly different angle. Thus, the same material will give a different diffraction pattern, depending on the detector used. Fortunately, this compression can be taken into account by using the Bragg equation for energy dispersive diffraction (12400/E=2 d sin θ) and remembering that the d spacing for the crystalline material is constant. This correction is given by:

$$E_{new} = \frac{E_{old}\sin\theta_{old}}{\sin\theta_{new}} \qquad (3)$$

where $2\theta_{old}$ is the Bragg angle for the collected data, $2\theta_{new}$ is the Bragg angle for the transformed data, $E_{old}$ is the energy value for the collected data, and $E_{new}$ is the desired value in the transformed system. To demonstrate how this transformation is applied, the peaks in the calculated patterns of FIG. 6 can be used. The most intense peak for the 3.0° Bragg angle spectrum is located at 62 keV. In the modified spectrum for 3.4° Bragg angle, the calculated position of the peak will shift to 55 keV in agreement with FIG. 6. In a similar way, the entire energy spectrum taken at any angle can be recalculated for the new Bragg angle.

In practice, if several detectors are used, all with different diffraction angles, a single reference angle is chosen. For example, in the aforementioned multidetector system, there are 12 detectors with Bragg angles ranging between approximately 2.9° and 3.4°. A reference angle of 3.0° is employed, and all 12 diffraction spectra taken at different angles will be modified by equation (3) to yield 12 spectra representing the spectra which would have been acquired if all of the detectors were positioned at angles of 3.0°. Recalculation and transformation to a common Bragg angle can be performed before or after the normalization procedures discussed above.

FEATURE EXTRACTION

The energy dispersive diffraction patterns or normalized spectra resulting from the steps described above can be displayed in graphical form and can be recognized by a human technician as indicating the presence of particular crystal structures representing a specific class of materials in the object. However, in an automatic method, the spectra must be evaluated on the basis of a predefined set of features which can be automatically extracted by a computer processing the spectra. The features extracted from those patterns should be sufficiently distinctive to permit accurate identification.

The simplest feature set is a listing of the positions (in keV) and the intensities of the strongest diffraction lines in the diffraction patterns. Examination of the PETN explosive diffraction pattern for example, reveals the following data:

| Peak Location (keV) | Relative Intensity |
| --- | --- |
| 26.53 | 9 |
| 31.40 | 28 |
| 37.60 | 9 |
| 46.15 | 100 |
| 50.34 | 77 |
| 53.19 | 6 |
| 71.46 | 4 |
| 73.63 | 10 |

This table can be stored in a library of standards along with many similar tables for other materials. Then, a similar table of peak positions and relative intensities can be extracted from the normalized spectrum for an unknown material. The peak positions and relative intensities can be supplied to any of the classification schemes discussed below.

The simple peak position and intensity method feature set discussed above can be useful for many simple materials under near-ideal conditions. However, in more complex situations where the patterns of two materials may be superimposed, a more comprehensive feature set gives better results. Thus, the feature extraction step can be expanded to provide a feature set which includes additional items. Among the features that we have found useful are:

peak positions
peak intensities
trough positions
trough intensities
centers of gravity of the spectrum within each of several preselected ranges of energies; and
the parameters of curves fit to the peaks, troughs or centers of gravity.

These features are shown schematically in FIG. 8. Spectrum 306 has a peak 308 with a position or energy level 310 and with an intensity level 312 Trough 314 also has an energy level and an intensity. The energy range which encompasses the useful portion of the diffraction spectrum is subdivided into several preselected energy ranges or "bins" 316a through 316e. In the particular arrangement illustrated, the energy ranges of the various bins are of equal magnitude. Thus, the spectral range of 20 to 120 keV is broken into five energy ranges, each 20 keV wide. The "center of gravity" or centroid 318 of that portion of the spectrum lying within each energy range is determined. The centroid has an intensity value equal to the mean intensity value within the energy range, and an energy value such that the area beneath the spectrum curve from the lower bound of the energy range to the energy value of the centroid is equal to the area beneath the curve from the energy value of the centroid to the upper bound of the energy range. That is, the integral of the intensity with respect to energy from the lower bound to the centroid is equal to the same integral from the centroid to the upper bound. The energy and intensity values of the centroids constitute useable features. One or more curves can be fit to the energy and intensity values of the various features mentioned above. Preferably, such a curve can be fit to the energy and intensity values of centroids 318. For example, a linear regression line 320 is fit to the centroids 318a–318e. The parameters of such a curve, such as the slope and intercept of regression line 320, provide an additional feature.

These features may be used in several combinations, although with different levels of success in matching various patterns. The combination that we have found to give the most accurate results are the energies and intensities of the five strongest peaks (10 features), the energies and intensities of five centroids of local energy bins (10 features) and the slope and intercept of the regression line describing the fit to the centroids (2 features).

A third approach to extract features from the diffraction data set is to focus on mathematical descriptions of the pattern as a whole rather than to focus on only a few obvious features. Preferably, the diffraction spectrum is subjected to a transformation which provides as its output a set of values such that each of the values depends, in some measure, on properties of the spectrum as a whole, rather than on individual features such as the position of a particular peak. One such method relies on a transformation of the spectrum into its cepstral representation. The cepstral representation includes an ordered set of cepstral coefficients defined by:

$$c(n) = \frac{1}{2\pi} \int_{-\pi}^{\pi} \log|X(e^{j\omega})| e^{j\omega n} d\omega \quad (4)$$

where $c(n)$ is the $n^{th}$ cepstrum coefficient, and $X(e^{j\omega})$ is the discrete Fourier transform of the diffraction spectrum $x(n)$. In other words, the cepstrum is the inverse Fourier transform of the logarithm of the absolute value of the Fourier transform of the diffraction spectrum. In deriving the cepstral representation, we treat the spectrum as a if it were a time domain signal.

Figure 9A:
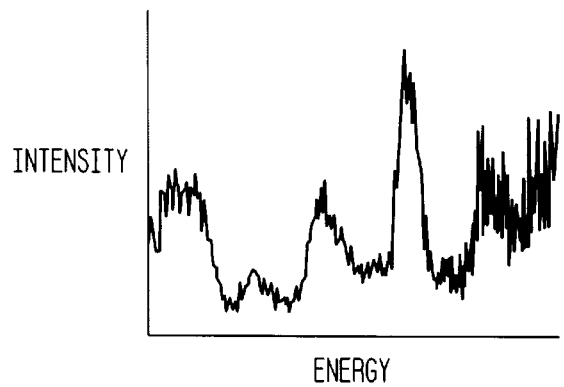
FIG. 9A is a graph of a diffraction spectrum.
Figure 9B:
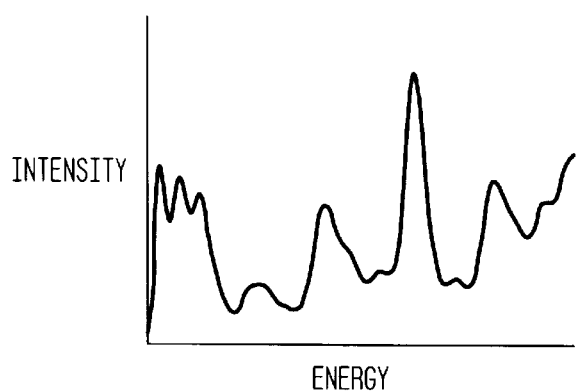
FIG. 9B is a graph of the diffraction spectrum of FIG. 9a after transformation and reconstruction from the transformed spectrum.

This process allows us to separate the underlying envelope of the spectrum from the original noise-corrupted spectrum. FIG. 9A shows a typical 512 point spectrum from a nonexplosive crystalline material. FIG. 9B shows the corresponding spectrum reconstructed from the lower forty cepstral coefficients, i.e., c(0) to c(40). Note that using these forty coefficients retains the underlying shape of the spectrum while the extraneous noise is removed. The underlying shape of the spectrum contains the useful information which can be used to classify the spectrum as representing one or another class of crystal structures. The noise details are not relevant to classification. Thus, forty lower-ordered cepstral coefficients constitute a sufficient feature set to classify the spectrum. This set of the forty lower ordered cepstral coefficients has been found to constitute a particularly effective feature set for many types of detection and classification problems as, for example, in determining whether or not a spectrum represents an explosive or a non-explosive material. However, other sets of cepstral coefficients can also be employed. For example, the lowest ordered coefficient c(0) may be omitted. Also, some of higher-ordered cepstral coefficients can be incorporated in the feature set. Note that because the cepstrum is based on the logarithm of the absolute value of the discrete Fourier coefficients, variations in peak intensity due to absorption or material variation are compressed and de-emphasized Other transforms, known as "homomorphic" transforms, which also incorporate a logarithmic transformation step, can provide similar insensitivity to absorption and material variation.

Still other transforms of the type known as linear orthonormal transforms can be applied to feature extraction from the full diffraction spectrum. One such linear orthonormal transform is the discrete cosine transform (DCT). The DCT is generally similar to the cepstral transform. However, the DCT and other linear transforms do not include the logarithmic function found in the cepstral transform. Therefore, the DCT and other linear transforms do not tend to suppress the distortions such as variations in peak heights due to noise and the presence of nearby amorphous materials to the same degree as the cepstral transform.

CLASSIFICATION

Once a feature set has been extracted from a diffraction spectrum, the feature set is used to classify the structural characteristics, of the object which produced the diffraction spectrum. For example, in examining a suitcase for the presence of explosives, a feature set may be derived from a spectrum which represents diffraction by a particular volume element within the suitcase. The classification step accepts the feature set and arrives at an indication as to whether the material in the particular volume element is or is not an explosive. Thus, the classification step determines whether or not the structure of the material, such as its crystal structure, belongs to the class of structures associated with explosives or to another class of structures associated with non-explosives. Alternatively, the information in the feature set can be used to classify the structure of the material as belonging to a particular class associated with a particular explosive.

The simplest form of automatic classification is a lookup and comparison scheme. Feature sets derived from known materials are stored, and the feature set derived from an unknown material is compared to each known feature set. For example, where the feature set consists of a table of peak energies and intensities, the table is compared to the corresponding tables for known materials. The material is classified as corresponding to the known material which has a table most closely matched to the table for the unknown material. Various rules for deciding which known table most closely matches the table for the unknown material may be employed. For example, in comparing a table of peak heights and intensities for an unknown material to a similar table for a known material, a mismatch in peak positions (energies) between known and unknown tables can be treated as more significant than a mismatch in heights (intensities) of the same peak in the known and unknown tables. The lookup and comparison scheme can also be applied to other feature sets discussed above.

Preferably, the classification step is performed by a probabilistic technique in which a plurality of features in the feature set contribute to the probability that the structure of the unknown material belongs to a particular class. Such a probabilistic technique relies on the feature set as a whole rather than on individual features. Although probabilistic classification techniques can include explicit, identifiable rules created by a programmer, the preferred techniques utilize a classification procedure which incorporates the results of training. For example, the classification algorithm can be used to process a training set consisting of feature sets for structures of known classification. The results of this processing are used to adjust the algorithm, so that the classification accuracy improves as the algorithm learns by processing the training sets.

One type of trainable classifier which can be employed is the artificial neural network. Various types of artificial neural networks can be employed. A particularly preferred form of artificial neural network known as a neural tree network is described in commonly assigned U.S. Pat. No. 5,634,087, the disclosure of which is incorporated by reference herein. The neural tree network as disclosed in the '087 Patent provides significant operational advantages such as ease of training and speed of operation. Other known types of neural networks, and other known forms of trainable classifiers also can be used. Indeed, using a given feature set, the same degree of classification accuracy can be achieved by many types of known trainable classifiers or neural networks. The training operation can be performed on one machine and the results can be replicated in additional machines. For example, training of a neural net results in a set of weight values defining the association between nodes of the net. This set can be recorded and incorporated in other, like nets.

The choice of features which are incorporated in the feature set will influence profoundly the accuracy achievable by a trainable classifier. Feature sets which incorporate features such as the peak positions, centroid positions and one or more curves such as a regression line fit to the centroids can provide useful accuracy. Whole-pattern feature sets, such as those incorporating cepstral or other transform coefficients as discussed above, in which each coefficient relates to the entire pattern of the spectrum, generally provide the best classification accuracy.

The output of the classification step for a particular volume element may be a "hard-limited" or binary indication as, for example, an indication that the particular volume element either does or does not have the structural features associated with the class of explosives. Alternatively, the output of the classification step may be a value such as a real number between zero and one indicating the degree of likelihood that the volume element has the structural features associated with explosives.

Although the particulars of the classifier or neural network may be generally conventional, the following discussion of neural networks is provided for the sake of completeness. Artificial neural networks attempt to model human biological neural networks to perform pattern recognition and data classification tasks. Neural networks are fine grain parallel processing architectures composed of non-linear analog processing units which attempt to replicate the synaptic-dendritic interconnections found in the human brain. The processing units typically accept several inputs and create a weighted sum (a vector dot product). This sum in then tested against the activation rule (typically a simple threshold) and then processed through the output function. The output function is usually a non-linear function such as a hard-limiter or a sigmoid function. The connectivity pattern defines which processing units receive the output value of a previous node as their input. At each instant of propagation, the values for the inputs define an activity state. The initial activity state is defined upon presentation of the inputs to the network. The output at any given activity state is derived from the state values which represent the inputs to all processing units and the values of the weights. The weights are chosen so as to minimize the error between the produced result and the correct result. The learning rule defines how to choose the weight values. Several commonly used learning rules are back-propagation, competitive learning, adaptive resonance, and self-organization.

Once the neural network learns the weights (can correctly identify the feature data in the training set), it is allowed to classify unknown feature data. If the neural network were subjected to sufficient training data, and the learning rule were appropriate, then sufficient generalization should have occurred to allow the unknown feature data to be correctly classified.

The use of the highly parallel architecture intrinsic to neural networks has several advantages over traditional von Neumann architectures. These advantages include excellent performance which yields rapid classification, simple and inexpensive processing units, modular structure, robustness to element failure, and adaptive training strategies.

Pattern recognition systems attempt to correctly classify data sets which are representative of a specific class as members of that class. The pattern recognition systems is typically separated into two main subsystems—feature selection and feature classification.

Feature classification is a technique which tessellates the feature space into generalized regions which represent every separable class. The tessellation is performed by finding n dimensional hyperplanes which are used to divide the feature space and isolate each class region. The equations for the hyperplanes are determined by finding the best coefficients (commonly known as weights) which separate the feature vectors. Once the tessellation is determined, classification is performed by taking the dot product of the feature vector with each tessellating hyperplane. This allows the feature vector to be placed on one side or the other of each tessellating hyperplane thereby uniquely placing the feature vector in one class region.

Several types of neurons and neural networks have been proposed. Most have tried to imitate the structure and functionality believed to be present in the human brain. None have yet achieved the performance of the human brain, but satisfactory (even exceptional) results have been obtained using these architectures on pattern recognition tasks. The most popular type of neuron due to its versatility and performance is the perceptron. Network architectures of these perceptrons, specifically multi-layer feedforward perceptron (MLP) networks, have been found to be very powerful and versatile due to the availability of efficient learning algorithms.

The MLP is the most widely studied and best understood architecture and therefore the most appropriate choice for determining preliminary classification performance. The major drawback to implementing MLP in hardware is the high cost of the parallel implementation, or conversely the slow processing speed of serial implementation.

The Neural Tree Network (NTN) has been studied as an alternative architecture. This tree structured neural network has significant implementation advantages and has been shown to provide performance equivalent to the MLP. It is therefore a viable alternative to the more computationally intensive approaches required by the MLP.

Although contemporary neural networks provide rigorous explanation for associative learning phenomenon, these systems have been restricted to learning specific tasks. Specifically, MLPs (Multi-Layer Perceptrons) have been widely employed for pattern classification tasks and provide a very simple feedforward structure for learning. The productivity of a neural network structure could be greatly enhanced if it would make use of past learning or experience. In essence, if we could model a system that could learn to learn then we would achieve better generalization and quicker learning.

To accomplish this goal, we have developed a model that is built to enhance retrainability and retention. The model (EGO: Error Gain Orchestrator) uses a network of neural network modules which exhibit a faster learning mechanism and allow for the incorporation of these features into Neural Tree Networks. The neural network is able to generalize and retrain on any material whose spectra has been experienced in the past training process. Thus, the network has retention to enable it to generalize well over similar materials. EGO is an attempt to capture this behavior by using modules of MLP, where each neuron element is controlled by a super neuron or neural network which is also another MLP. This super net consists of neurons that remembers the trajectory its neuron followed for learning a particular task or a series of similar tasks.

Iterative gradient descent algorithms like the LMS algorithm have been used to perform classification tasks which are linearly separable. For nonlinear classification an extension of this algorithm known as the backpropagation algorithm is used. The Backpropagation algorithm is used over a network or neurons in layers called MLPs (Multi-Layer Perceptrons).

The iterative learning is performed over a set of vectors, $X_i$, called the training set with which their desired outputs, $y_i$, have been specified. Typically these outputs are labels or classes into which the input vectors have to be classified. The iterative update generates a solution weight vector, $W_{opt}$, which minimizes the error between the desired output and the actual output. Backpropagation is widely used for several applications and is a perfect example of learning by example. The model that we use extends this approach to perform learning by learning.

Gradient descent algorithms provide an efficient procedure by taking a set of randomly initialized weights network and updating them iteratively to an optimum set of weights which minimizes the error for the entire neural network. The optimum set of weights provide an optimal or a pseudo-optimal solution to the problem it is trained on.

The basis of formulating the EGO lies in the choice of parameters in the learning rule that allows faster learning or faster convergence for a given problem and also limits these parameters to a finite range of values over a series of tasks. Faster learning can be achieved by adjusting the gain parameter in a way such that the weights approach the optimum the fastest by the following:

train the network to find a set of optimal weights, take the current weight vector in the weight update equation and find a pattern vector whose resultant with the current weight vector yields a vector whose angle with the optimum weight vector is the minimum. Hence we try to find the best pattern vector from the training set which yield the next weight vector in the update equation which is the nearest to the optimum.

Since the backpropagation rule is used for MLPs, every hidden node will have its own optimum step size corresponding to the optimum weight vector summed at that node. We consider this vector approach only from the input layer to the hidden layer. However, this metric could also be used between the hidden and output layers, if we consider the outputs of the hidden node as a feature vector.

The previous paragraph explained the metric used to modify the update rule to achieve faster convergence. This training is performed when the optimum weight vector is known. In order to remember the trajectories of this fast convergence we should adopt a mechanism where the neural network will achieve comparable performance when the optimum weights vector is not known. To achieve this we train a super net for every neuron in the hidden layer. This super net is trained to learn the step sizes generated from the modified update rule. The input pattern to the super net is the current weight vector $W_t$ in the update equation and the best pattern vector $X_p$ chosen from the training set.

The Super Net is trained over several weight sets and their desired optimal step sizes found by the metric explained above. After the Super Net has been trained, we embed this network in a normal MLP to guide each of its hidden nodes to convergence. Typically, each hidden node will have its corresponding super net which has been trained to remember the trajectories of convergence the hidden node has experienced.

Both the neural tree network (NTN) and the multilayer perceptron network (MLP) have been used for the pattern recognition of the EDXD spectra with equally high reliability. The primary difference between the two lies in the ability to implement the algorithms in hardware.

POSTPROCESSING

The error rate of identification of EDXD diffraction patterns by an efficient classifier such as a multilayer feed-forward perceptron (MLP) or neural tree network (NTN) utilizing an efficient feature set such as the cepstrum representation is approximately 0.5% or less. That is, where the classifier provides a binary indication as to whether explosives are or are not present in a particular volume element based on the diffraction spectrum for that volume element, that indication will be incorrect for 0.5% or less of the volume elements. While this seems like a good result, approximately 1,000 to 2,000 volume elements are examined during examination of a sizable solid object such as a suitcase. With an error rate of 0.5% examination of a typical suitcase devoid of explosives would result in approximately 10–20 false positive indications of explosive presence in individual volume elements. The postprocessing step evaluates the local information obtained for each volume element, such as an indication that an explosive is present, in conjunction with local information derived for adjacent volume elements. This effectively combines local information for a plurality of adjacent volume elements into a larger determination as to whether explosives are present in the area. A real mass of explosives normally will extend to several adjacent volume elements, and would normally yield positive indications with respect to several adjacent volume elements. By contrast, false alarms occur in a widely dispersed pattern. Thus, by evaluating groups of adjacent volume elements together, the method can reject false indications.

Figure 4B:
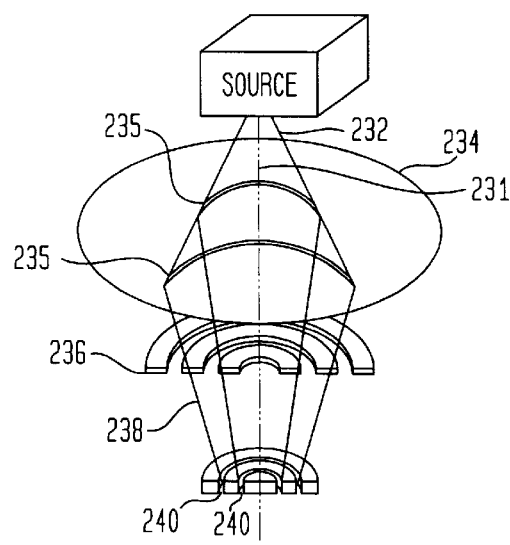
FIG. 4B is a diagrammatic view depicting further apparatus usable in methods according to further embodiments of the invention.

As schematically depicted in FIG. 4B, the volume element or region 235 which is "seen" be a particular detector 240, and which contributes to an x-ray diffraction spectrum taken at a particular position of the object, may be an annulus rather than a point. As the annular region sweeps through the object, it will have a greater probability of intercepting embedded masses such as embedded explosive masses than a smaller region. This effect can be visualized by imagining an attempt to observe a small spot on a wall by sweeping a flashlight beam across the wall; a wide beam will have a greater probability of hitting the spot than a narrow, pinpoint beam. A computer analysis of this effect shows that there is a "halo" effect when the incident EDXD x-ray beam interacts with the embedded mass. The net effect of this halo is to enlarge the apparent volume of the explosive to approximately three times its true size. This has two important ramifications. First, even a small object volume (for example a small bomb) is magnified to a larger size, thus increasing its probability of detection. Second, the halo causes a large number of neighboring voxels to become positive. Thus, if a single voxel is identified as positive, we can reject it as a false alarm. A "true" explosive detection event must have several of its nearest neighbors that are also positively identified. This is the basis of the nearest neighbor correlation. Also, since a true explosive would occupy several neighboring volume elements, there would be a very large number of voxels identified as positive.

Figures 10A, 10B, 11:
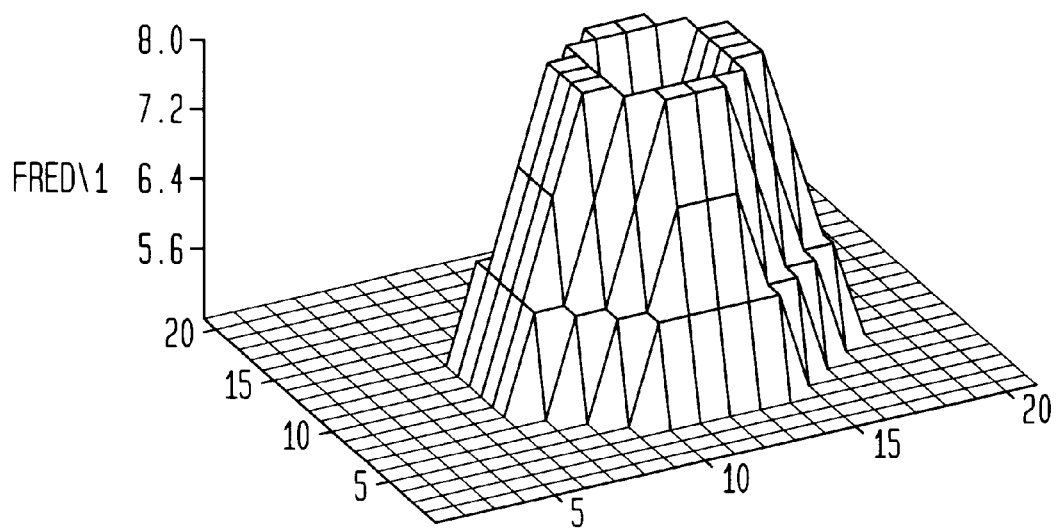
FIG. 10A is a cross-sectional diagram of an x-ray beam.
FIG. 10B is a representation of an object embedded in a surrounding space.
FIG. 11 is a graph depicting a pattern of convolution resulting from interaction between the beam of FIG. 10a and the object of FIG. 10b.

The origin of the "halo" effect is illustrated in FIG. 10A, where the annular region 235 is represented by zeros and ones representing the absence or presence respectively, of x-ray intensity at any spatial point. The points marked with ones are included in the annular region 235, whereas the points marked with zeros are not included in the annular region. FIG. 10B shows a representation of a solid explosive. The points occupied by the explosive are denoted by ones. For purposes of demonstration, we assume that the explosive to be detected is small (3×3 elements) compared to the x-ray beam (8×8 elements). As the x-ray beam sweeps past the crystalline object, the apparent size of the object increases because of the convolution of the two shapes. The result is shown in FIG. 11. In FIG. 11, the horizontal axes represent position of the beam relative to the object. The vertical axis represents the number of "hits" or instances in which a part of the annular region intersects a part of the explosive. Note that the region with a non-zero number of hits is considerably larger than the 3×3 object. The effect is to increase the apparent size of the object to be detected.

In evaluating the local information such as indications of explosive presence for each voxel in conjunction with the local information for other voxels, the method can use algorithms of the type commonly referred to as "erosion" and "dilation". In erosion, the system selects a given voxel having local information which indicates presence and examines the original local information in a two-dimensional or three-dimensional array of voxels surrounding a given voxel. If the original local information in the other voxels of the array meets a predetermined test demonstrating that the local information in the other voxels of the array also indicate presence, the local information in the given voxel is retained. If the local information in the other voxels of the array does not meet the test, the local information in the given voxel is altered to delete the indication of presence.

Figures 12A, 12B, 13:
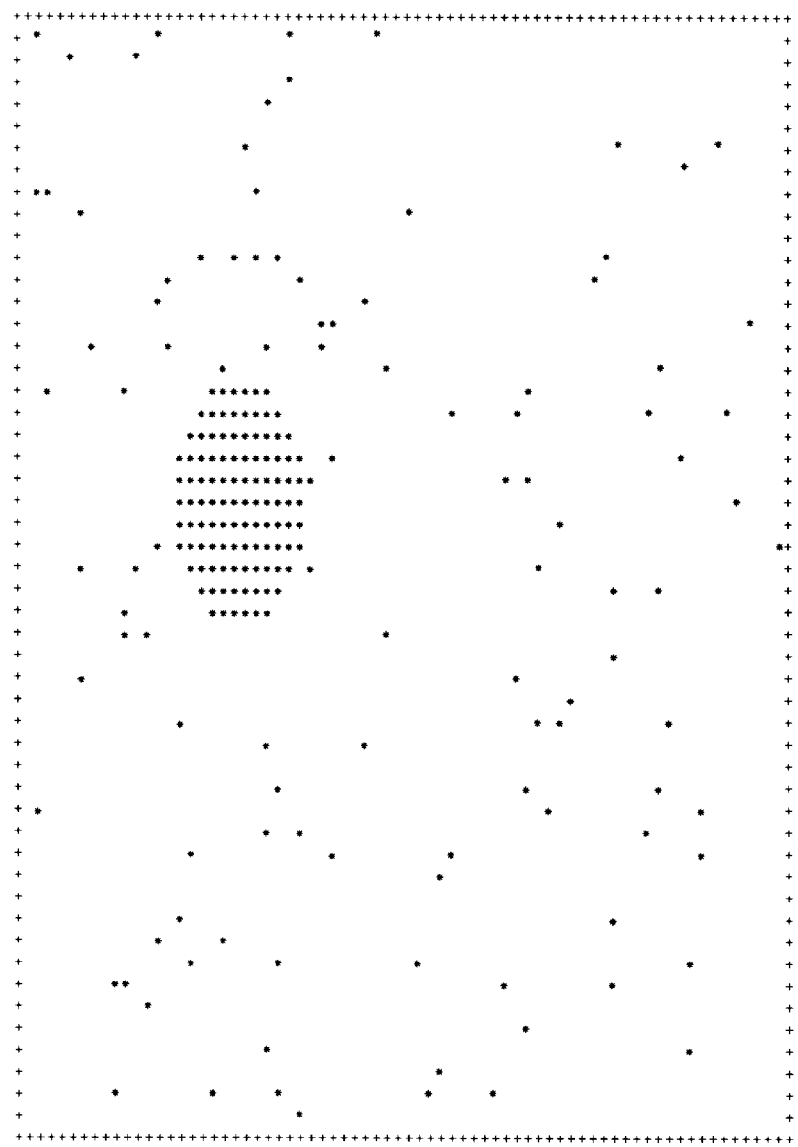
FIGS. 12A and 12B are diagrams depicting arrays of volume elements and binary presence data associated therewith.
FIG. 13 is a graph depicting presence data obtained by evaluation of individual volume elements in an object containing a mass of a contraband material.

For example, in a binary system the local information for each voxel provided by the classifier may be a "1" indicating presence of a structure of the class associated with explosives or a "0" indicating absence of such a structure. The test may be set so that in a two dimensional N×N array of voxels surrounding the given voxel, at least m voxels must have a "1" as local information. One such system, using an 3×3 array with m=5 is shown in FIGS. 12A and 12B. In FIG. 12A, the given voxel at the center of the diagram, has local information of "1", whereas the other voxels in such array have local information of "0". The local information in the given voxel is changed to "0", and hence the original indication of presence in the given voxel is suppressed. In FIG. 12B, 5 of the 8 voxels in the 3×3 array surrounding the given voxel have local information of "1", and hence the original local information "1" in the given voxel remains unchanged. This process is repeated for each voxel where the original local information is "1", until all voxels having an original "1" have been tested. In each case, the local information used in applying the test is the original local information. Thus, if the local information in any of the voxels surrounding the given voxel has been changed, that changed information is ignored. The net result of the process is to wipe out isolated presence indications. The process can be repeated, using the remaining original and changed local information as a new set of original information.

The erosion scheme for binary presence information can be varied by changing the array size and the test. For example, the test criterion can be altered by varying the value of m. Thus, if m=1 the original local information is retained if any one voxel in the surrounding array is a 1. Also, the erosion process can be applied to a three-dimensional array, so that the N×N×N array of voxels surrounding the given voxel is examined in the same way as discussed above. The reverse process, known as dilation, examines a given voxel having original local information which indicates absence of the selected class of structures, tests the adjacent voxels, and modifies the given voxel if the local information in the adjacent voxels do not also indicate absence.

Similar techniques can be applied to non-binary presence indications such as real numbers indicative of the likelihood that a particular structure is present. The term "grey scale" is sometimes used to describe such a numerical indication. Grey scale dilations and erosions involve ordering the amplitudes of voxels (2D) or voxels (3D in a neighborhood (such as an N×N or N×N×N array) from lowest to highest and replacing the amplitude of the voxel in the center of the neighborhood with the amplitude of one of the other voxels (or a function of the amplitudes of a subset of the voxels) in the neighborhood. Examples include the MIN filter (grey scale erosion) where the central voxel amplitude is replaced with the minimum amplitude in the neighborhood, the MAX filter (grey-scale dilation) where the central voxel amplitude is replaced with the maximum amplitude in the neighborhood and the Median filter where the central voxel amplitude is replaced with the median amplitude in the neighborhood. These non-linear filters are very powerful and have the advantage over linear, correlation type filters that compute a weighted sum of all of the voxels in a neighborhood in that they do not blur the edges of objects. They are used frequently for "noise cleaning" when the noise consists of isolated spikes (voxels that are very different in amplitude from most of their neighbors).

A further process, referred to as linear correlation can also be used. In a linear correlation filter, the value of a weighted sum of the local information in voxels in the neighborhood is tested and the value of the local information in the central pixel is retained only if the weighted sum indicates that the value of the local information in the central pixel is well-correlated with the local information in the other voxels in the surrounding neighborhood. The linear correlation process as applied to binary information reduces to the erosion and dilation processes discussed above. Accordingly, those processes are sometimes referred to as "nearest neighbor correlation".

A number of different postprocessing operations using different techniques can be applied in parallel. For example, a dilation scheme using two-dimensional voxel arrays can be applied on several different sets of two-dimensional voxel arrays representing sets of parallel slices through the object at different inclinations. This further enhances the ability of the system to detect thin sheets or strings of contraband. Also, both two and three dimensional schemes can be applied in parallel. If an embedded mass of contraband remains after either postprocessing step, the system treats it as a real mass and initiates an alarm.

After postprocessing to eliminate false positive indications the explosive image size and location are found. An alarm signal is initiated if any explosive mass remains at this stage. The center is defined and the ellipse that defines the area of the explosive is also determined. In a simulation, false alarms are defined by anything that lies outside of this ellipse. The number of false alarms both before and after post-processing are found as well as the total number of hits in both cases.

Figure 14:
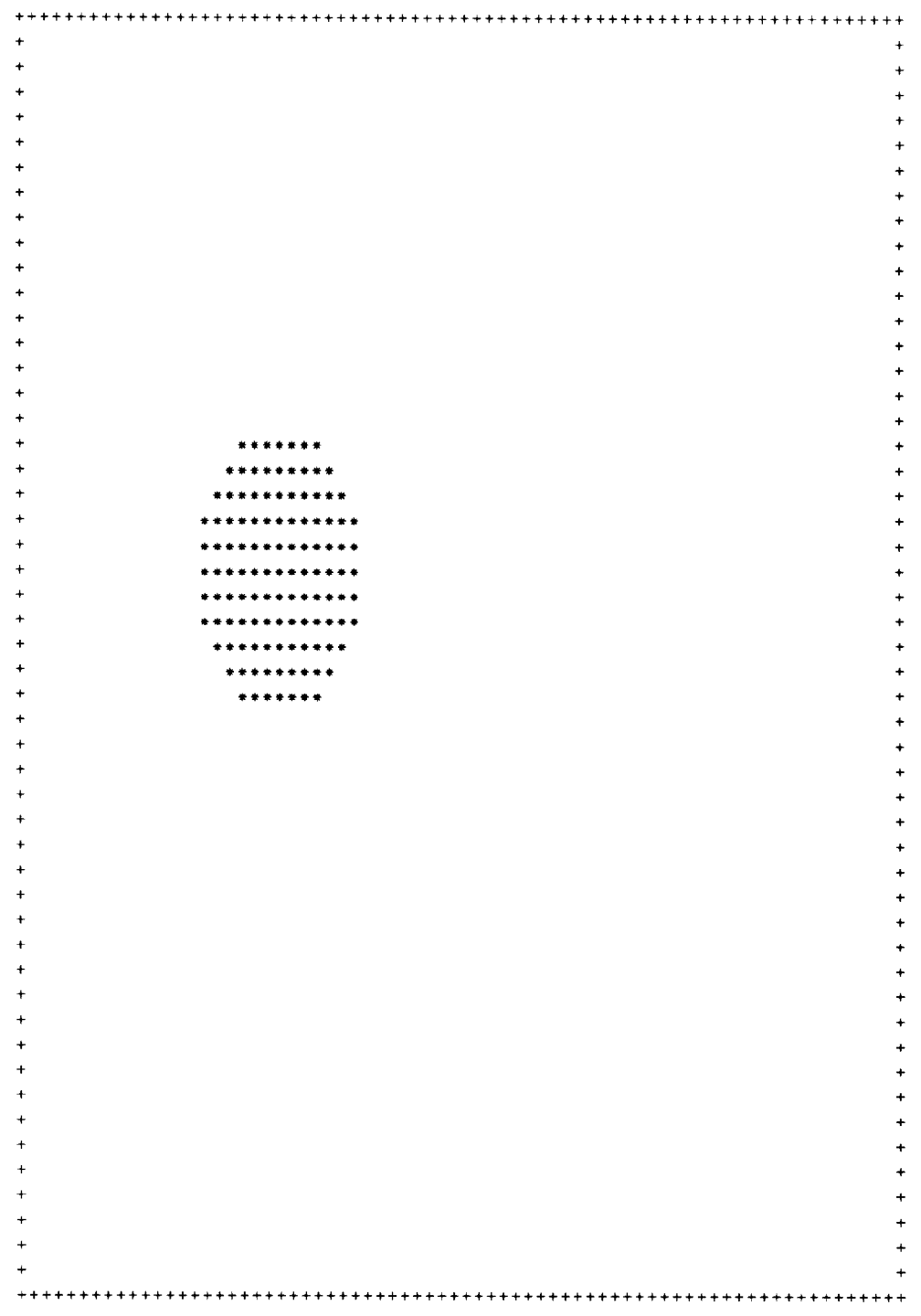

FIGS. 13 and 14 show the pre- and post-correlation arrays for a typical simulation of an explosive of 3×3 units, using binary presence indications and erosion with a two-dimensional 3×3 array and m=5, as discussed above with reference to FIGS. 12A and 12B. In FIGS. 13 and 14, an asterisk indicates local information with a positive indication of presence. The 3×3 explosive is a "typical" sized explosive in the sense that it occupies an area less than ½ the beam diameter of 50–100 mm. It can be seen from these figures that the correlation does indeed eliminate all the false alarms. An additional 900 trials were run and pre- and post-correlation false alarms were counted for a 3×3 explosive. The result in every case was no false alarms after correlation. Other experiments were run for a variety of explosive configurations (rods and sheets) and in each the result was the same as for the 3×3. From these results it can be seen that the correlation method is an excellent way to eliminate false alarms in the NTN or MLP data.

DETECTION OF COUNTERMEASURES

One of the principal uses of the tomographic EDXD method is for the detection of explosives, illicit drugs, and other contraband. Therefore, we must be concerned with attempts to hide the target materials. The two principal countermeasures are masking (hiding the target in a heavy absorber) and mixing (adding a second crystalline material to confuse the neural network). Fortunately, the multidetector EDXD system is capable of detecting either of these countermeasure as described below.

Masking can be detected by examining the intensity of the direct beam after it passes through the obscuring object hiding the contraband material. Since the incident beam operates at 160keV, it can penetrate objects such as luggage and parcels. Therefore, any heavy masking agent that is blocking the diffracted x-ray beam will also block a significant portion of the incident beam. Thus, masking agents can be detected by constant monitoring of the transmitted beam. Recall that this is done routinely for purposes of normalization and so, this information is already available.

Mixing of the crystalline contraband material with another crystalline material will produce a superposition of the two diffraction patterns. Therefore, the neural network or other classifier should be designed to recognize this possibility as a possible countermeasure. This is difficult to do if the feature set that is extracted from the data consists of only peak positions and intensities. However, a more robust feature set such as those described above using transform coefficients such as a cepstral representation, or using the centroids and regression lines, allow the classifier to detect mixing.

SECONDARY CONTRABAND SIGNATURES

In addition to the diffraction patterns described above, the EDXD process provides other information to help detect the presence of contraband material. This is of special importance for the detection of explosives where the device must also have a detonator and energy source that may also yield useful information. Of particular interest is the fact the EDXD diffraction pattern will also contain chemical signatures in the form of fluorescent lines. These lines are much sharper than the diffraction lines and as a result, can be easily separated. Moreover, each element yields a unique set of characteristic radiation lines and suspicious materials can be easily identified. As an example, lead, mercury, cadmium, and other heavy materials are routinely used in batteries, switches, or detonators. Thus, secondary information is available that will help identify suspicious objects. This method is most useful for heavy metals.

EXAMPLES

The following non-limiting examples illustrate certain features of the invention:

Example 1

Energy dispersive diffraction data was taken with a tungsten x-ray source operating at 160 keV with only a single detector monitoring the diffracted beam. An unknown explosive material was placed into the beam and the five strongest diffraction lines were extracted after masking the tungsten characteristic lines. The energies and relative intensities of these lines were 46.7 keV (100%), 32.4 keV (70%), 74.0 keV (26%) 41.8 keV (17%), and 36.4 keV (10%). We can identify this material by examining the five strongest lines of suspected reference standards as summarized in the following table:

| Material | Five Strongest Lines - keV (% Intensity) | | | | |
|---|---|---|---|---|---|
| C4 | 73.6 (100) | 35.6 (88) | 26.4 (78) | 71.1 (56) | 30.4 (29) |
| PETN | 46.2 (100) | 50.3 (77) | 31.4 (28) | 73.6 (10) | 26.5 (9) |
| RDX | 34.9 (100) | 26.3 (82) | 43.6 (78) | 40.5 (69) | 73.5 (35) |
| Semtex | 26.4 (100) | 73.6 (88) | 34.6 (87) | 71.3 (36) | 83.2 (16) |
| TNT | 46.5 (100) | 32.2 (93) | 41.8 (30) | 73.8 (15) | 36.4 (14) |

By comparing the diffraction lines with those of the standards in the above table, it should be apparent that the unknown material is most likely TNT due to the close match in the peak position. Note however, that several of the relative intensities of the unknown do not match the standard within the experimental error. As noted before, any discrepancy in the intensity values is likely due to absorption, changes in tube characteristics or material variations. Therefore, the intensity comparison should be used only as a secondary match. In the present case, the difference in intensity between the reference and test samples was the very large grain size (up to 1 mm) of the unknown compared to the fine powder of the reference standard.

Example 2

Energy dispersive diffraction data was taken with a tungsten x-ray source operating at 160 keV with only a single detector monitoring the diffracted beam. An unknown explosive material was surrounded by a heavy absorber and was placed into the beam. The five strongest diffraction lines were extracted after masking the tungsten characteristic lines. The energies and relative intensities of these lines were 46.5 keV (100%), 73.8 keV (63%), 32.1 keV (29%) 41.6 keV (19%), and 36.2 keV (7%). When we try to identify this material by comparison with the table in Example 1, we find that the peak positions once again match those for TNT, but this time, there is a much larger discrepancy between the observed and the expected intensity values. In particular, the low energy peak at 32.1 keV has decreased from the expected 93% to only 29%. Also, the high energy peak at 73.8 keV has increased from 14% to 63%. All of these observations are consistent with the nonlinear absorption process discussed earlier. We can correct for this absorption by normalizing the data with the direct beam. After this is done, the values for the peak intensities much more closely match the expected values as shown in the table below:

| Material | Five Strongest Lines After Normalization - keV (% Intensity) | | | | |
|---|---|---|---|---|---|
| TNT | 32.1 (100) | 46.5 (43) | 36.1 (20) | 41.5 (19) | 73.8 (8) |
| unknown | 32.1 (100) | 46.5 (30) | 35.9 (24) | 41.6 (14) | 73.8 (12) |

The agreement between the experimental data and the standard is now much better than before normalization was done. As a result, our confidence in the match has increased. Note also that the relative intensities of the standard change when normalization is performed.

Example 3

The EDXD diffraction pattern shown in FIG. 15 was obtained at a Bragg angle of 3.2°. From this data, a feature set was extracted consisting of five peak positions and intensities, five centers of gravity of local energy bins, and the regression line for these centers of gravity. These twenty two features were analyzed with an MLP neural network which had been trained on several thousand patterns of ten explosives (C4, Detasheet, Dynamite, HMX, Picratol, RDX, Semtex 'A', Semtex 'H', and TNT.) With these twenty-two features, the neural network was able to correctly identify this material as TNT. With fewer than twenty-two features, the error rate starts to increase to an unacceptable level.

Example 4

The EDXD diffraction pattern shown in FIG. 16 was obtained at a Bragg angle of 3.2°. The material under test was a powder form of PETN, which had been deliberately diluted by a nonexplosive (sodium bicarbonate). Also, the diluted mixture was placed behind a thick absorber. From this data, a feature set was extracted consisting of five peak positions and intensities, five centers of gravity of local energy bins, and the regression line for these centers of gravity. These twenty two features were analyzed with an MLP neural network, which had been trained on several thousand patterns of ten explosives (C4, Detasheet, Dynamite, HMX, PETN, Picratol, RDX, Semtex 'A', Semtex 'H', and TNT.) With these twenty-two features, the neural network was able to correctly identify this material as PETN.

Example 5

EDXD diffraction patterns were obtained with a multidetector tomographic system at a nominal Bragg angle of 3.0° for C4, Detasheet, Semtex A, Semtex H explosives. The incident x-ray beam was also collected through a pinhole aperture. From this data, a neural tree network ("NTN") was trained using a feature set composed of the cepstral features. Once the network was trained, additional diffraction patterns were taken and submitted to the neural network for analysis. The identification accuracy of the NTN depended on the number of cepstral features used. In general, the accuracy of identification increased as the number of features increased as shown in FIG. 17.

Example 6

EDXD diffraction patterns were obtained with a multidetector tomographic system at a nominal Bragg angle of 3.0° with 3 seconds counting time. The object being interrogated was a large suitcase with approximate dimensions of 550' 650' 300 mm. Inside the suitcase were placed three separate pieces of C4 explosive. After data collection was completed, the data were normalized and the feature extraction was based on the lower 26 cepstral coefficients. These features were then analyzed with a hard limited neural tree network. The detection results are shown in FIG. 18A. Each asterisk represents a detection event, i.e. a volume element for which the NTN yields local information with a positive indication of explosive presence. After the NTN output data is analyzed by the erosion process as process described above. The erosion process uses a 3×3×3 array and m=13, i.e., the positive indication of explosive in the center voxel is eliminated unless positive indications also present for 13 of the 26 surrounding pixels. The false alarms are eliminated as shown in FIG. 18B. This process correctly identified not only the presence and the location of the explosives, but also the chemical composition of the hidden explosive charges.

Example 7

The EDXD diffraction pattern shown in FIG. 19 was obtained at a Bragg angle of 3.2°. The material under test was a powdered form of RDX which had been deliberately sealed in a lead foil bag to simulate a potential countermeasure. Note in the diffraction pattern that the features of the RDX explosive are still evident even though there is high absorption of the low energy end of the spectrum. Of even greater note is the fact that lead fluorescence lines are evident at 71.5 and 73.6 keV. Thus, the EDXD pattern also can contain fluorescence information that is helpful in assessing a threat.

Example 8

EDXD diffraction patterns were obtained with a multidetector tomographic system at a nominal Bragg angle of 3.0° with 3 seconds counting time. The object being interrogated was a large suitcase with approximate dimensions of 550× 650×300 mm. Inside the suitcase were placed three explosive blocks. After data collection was completed, the data were normalized and the feature extraction was based on the lower 26 cepstral coefficients. These features were then analyzed with a hard limited neural tree network. The detection results were then correlated subjected to erosion as described in Example 6 to remove false positive local information. The results are shown in FIG. 20 where the three explosive charges are represented as oblate spheroids. In addition, the tomographic EDXD system also found a very dense absorber shown as a rectangular block in the lower right corner of the suitcase. This absorber was detected by monitoring the direct (transmitted) beam, which in this case dropped almost to zero. Since the direct beam is capable of penetrating most objects found in a suitcase, it was concluded that this absorber was intended as an attempt to hide something. While the EDXD system could not identify the material inside the absorber, the system was able to indicate a possible threat.

What is claimed is:

1. A method of examining crystal structure of an object by energy dispersive x-ray diffraction comprising the steps of:
   (a) applying a beam of incident X-ray radiation, detecting diffracted X-ray radiation and deriving an energy spectrum of the diffracted X-rays from said object;
   (b) extracting a plurality of features from said spectrum constituting a feature set; and
   (c) classifying the structure of the object by a probabilistic technique wherein a plurality of said features in said feature set contribute to the probability that the structure of the object belongs to a particular one of a plurality of classes.

2. A method as claimed in claim 1 wherein said classifying step includes the step of subjecting said features in said feature set to processing in a classifier which incorporates the results of training using one or more energy spectra representing X-rays diffracted by one or more known substances.

3. A method as claimed in claim 2 wherein said classifier includes a multilayer perceptron network.

4. A method as claimed in claim 2 wherein said classifier includes a neural tree network.

5. A method as claimed in claim 1 wherein said feature set includes features selected from the group consisting of:
   (i) energy and intensity values of peaks;
   (ii) energy and intensity values of troughs;
   (iii) energy and intensity values of centroids of regions of the spectrum lying within preselected ranges of energies; and
   (iv) parameters of one or more curves of intensity versus energy fit to at least some of said energy and intensity values.

6. A method as claimed in claim 5 wherein said feature set includes energy and intensity values of a predetermined number of peaks having the greatest intensity values, energy and intensity values of centroids of regions of the spectrum in a predetermined number of equal portions of the range of energy encompassed by the entire spectrum, and a slope and intercept of a straight line curve of intensity versus energy fit to the energy and intensity values of said centroids.

7. A method as claimed in claim 6 wherein said predetermined number of peaks is five and said predetermined number of equal portions is five.

8. A method as claimed in claim 1 wherein said step of extracting set of features from said spectrum includes the step of applying a transform to said spectrum so as to provide a set of coefficients such that each said coefficient depends on the entirety of said spectrum, said set of features including at least some of said coefficients provided by said transform.

9. A method as claimed in claim 8 wherein said transform is a homomorphic transform.

10. A method as claimed in claim 9 wherein said transform is a cepstrum transform yielding an ordered set of cepstral coefficients and wherein the set of features includes a set of cepstral coefficients.

11. A method as claimed in claim 10 wherein said set of features consists entirely of said cepstral coefficients.

12. A method as claimed in claim 8 wherein said transform is a discrete cosine transform.

13. A method as claimed in claim 1 wherein said classifying step is performed so as to provide structure classification information representing the likelihood that said object contains any of several known contraband substances.

14. A method as claimed in claim 13 wherein said contraband substances are illegal drugs.

15. A method as claimed in claim 1 wherein said classifying step is performed so as to provide structure classification information representing the likelihood that said object contains any of several known explosives.

16. A method as claimed in claim 15 further comprising the step of examining said spectrum to detect fluorescence peaks associated with heavy metals.

17. A method as claimed in claim 1 wherein said classifying step is performed so as to provide structure classification information representing the likelihood that said object contains each one of several known crystalline explosives.

18. A method as claimed in claim 1 wherein said classifying step is performed so as to provide structure classification information representing the likelihood that said object contains one or more contraband materials, the method further comprising the step of monitoring the x-ray absorptivity of the object and providing an indication that countermeasures have been employed to conceal the contraband materials if the absorptivity exceeds a limit value.

19. A method as claimed in claim 18 wherein said step of monitoring the absorptivity of the object includes the step of monitoring the intensity of that portion of the incident beam transmitted directly through the object.

20. A method as claimed in claim 1 wherein said applying, extracting and classifying steps are performed separately on each of a plurality of volume elements in the object so as to provide local structure classification information with respect to each said volume element.

21. A method as claimed in claim 20 wherein the local information provided by said classifying step with respect to each said volume element includes an indication of whether a substance of a preselected class is present in such volume element, the method further comprising the step of filtering the local information with respect to spatial frequency in the frame of reference of said volume elements so as to suppress local information having a spatial frequency higher than a predetermined frequency.

22. A method as claimed in claim 20 wherein the local information provided by said classifying step with respect to each said volume element includes an indication of whether or not a substance of a preselected class is present in such volume element, the method further comprising the step of evaluating the local information obtained with respect to adjacent volume elements in conjunction with one another.

23. A method as claimed in claim 22 wherein said evaluating step is performed so as to suppress indications that a substance of such class is present in isolated volume elements remote from other volume elements having indications that such substance is present.

24. A method as claimed in claim 20 wherein said classifying step yields a binary presence value indicating whether or not a substance of a preselected class is present in each said volume element, the method further comprising the step of testing the binary indication for a given volume element to determine whether a predetermined number of voxels within a preselected distance from the given volume element have the same binary indication, and suppressing the binary indication for the given volume element if less than said predetermined number of voxels within the preselected distance have the same binary indication.

25. A method as claimed in claim 24 wherein said testing step includes examining nearest neighbor volume elements to the given volume element.

26. A method as claimed in claim 25 wherein said testing step includes determining whether a majority of the nearest neighbor volume element to the given volume element in an array have the same binary value.

27. A method examining crystal structure of an object comprising the steps of:
  (a) obtaining structural information with respect to each of a plurality of volume elements in the object;
  (b) classifying the structural information so as to provide a separate indication with respect to each said volume element as to whether a substance of a preselected class is present in such volume element; and
  (c) evaluating the indications obtained with respect to adjacent volume elements in conjunction with one another so as to suppress indications that a substance of such class is present in isolated volume elements remote from other volume elements having indications that such substance is present.

28. A method as claimed in claim 27 wherein said evaluating step includes the step of applying an erosion process to said indications.

29. A method as claimed in claim 28 wherein said evaluating step includes the step of applying a plurality of different erosion processes to said indications.

30. A method as claimed in claim 30 wherein said plural erosion processes include a plurality of two-dimensional erosion processes using planar arrays of volume elements, the planar arrays of volume elements used in different ones of said plural erosion processes lying planes having different orientations.

31. A method as claimed in claim 28 wherein said erosion process is a three-dimensional erosion process.

32. A method as claimed in claim 27 wherein said indication with respect to each said volume element is a binary presence value indicating whether or not a substance of said preselected class is present in each said volume element, said filtering step including the step of testing the binary indication for a given volume element to determine whether a predetermined number of voxels within a preselected distance from the given volume element have the same binary indication, and suppressing the binary indication for the given volume element if less than said predetermined number of voxels within the preselected distance have the same binary indication.

33. A method as claimed in claim 32 wherein said testing step includes examining nearest neighbor voxels to the given volume element.

34. A method as claimed in claim 33 wherein said testing step includes determining whether a majority of the nearest neighbor voxels to the given volume element in a two-dimensional array have the same binary value.

35. A method as claimed in claim 27 wherein said structural information for each said volume element includes an energy spectrum of X-rays diffracted by material in such volume element.

36. A method as claimed in claim 27 wherein said structural information for each volume element includes one or more values of the X-ray absorptivity of the material in such volume element.

37. A method as claimed in claim 27 wherein said step of obtaining structural information includes the step of examining the object by one or more techniques selected from the group consisting of nuclear resonant absorption, pulsed fast neutron analysis, thermal neutron analysis, computed X-ray tomography, X-ray backscatter imaging and Compton scatter imaging.

38. A method of examining an object by energy dispersive x-ray diffraction comprising the steps of:
  (a) applying an incident beam of X-ray radiation to an object;
  (b) detecting diffracted X-rays from said incident beam diffracted by the object over a range of Bragg angles greater than zero, and obtaining an uncorrected spectrum of said diffracted X-rays, whereby said uncorrected spectrum will include the true diffraction spectrum of the object convolved with the spectrum of the incident beam, absorption by the object and a broadening effect caused by said non-zero range of Bragg angles;
  (c) deriving a raw transmission spectrum, including the spectrum of the incident beam with the effect of absorption by the object;
  (d) subjecting said raw transmission spectrum to an algorithm simulating convolution of said raw transmission beam spectrum with said broadening effect to obtain a modified transmission spectrum; and
  (e) obtaining a normalized spectrum by dividing said uncorrected spectrum by said modified transmission spectrum.

39. A method as claimed in claim 38 wherein said step of deriving a raw transmission spectrum includes the step of detecting transmitted X-rays from said incident beam which pass through said object undiffracted.

40. A method as claimed in claim 38 wherein said algorithm includes convolution of each data point in the raw transmission spectrum by a Gaussian broadening curve.

41. A method as claimed in claim 40 further comprising the step of determining an exponent of said Gaussian broadening curve by comparing the breadth of at least one peak in said uncorrected spectrum with at least one peak in a spectrum of said incident beam or in said raw transmission spectrum.

42. A method of examining an object by energy dispersive x-ray diffraction comprising the steps of:
   (a) applying an incident beam of X-ray radiation to an object;
   (b) detecting diffracted X-rays from said incident beam diffracted by the object over a range of Bragg angles greater than zero, and obtaining an uncorrected spectrum of said diffracted X-rays, whereby said uncorrected spectrum will include the true diffraction spectrum of the object convolved with the spectrum of the incident beam, absorption by the object and a broadening effect caused by said non-zero range of Bragg angles;
   (c) deriving a raw transmission spectrum including the spectrum of the incident beam with the effect of absorption by the object;
   (d) obtaining a modified diffraction spectrum by subjecting said uncorrected spectrum to a deconvolution algorithm effective to substantially reverse said broadening effect; and
   (e) obtaining a normalized spectrum by dividing said modified diffraction spectrum by said raw transmission spectrum.

43. A method as claimed in claim 38 or claim 42 further comprising the step of examining the normalized spectrum to derive an indication of the crystal structure of the object.

44. A method as claimed in claim 43 wherein said step of examining the normalized spectrum includes the steps of extracting a plurality of features from said normalized spectrum constituting a feature set; and classifying the structure of the object by a probabilistic technique wherein a plurality of said features in said feature set contribute to the probability that the structure of the object belongs to a particular one of a plurality of classes.

45. A method as claimed in claim 1 wherein said step of extracting set of features from said spectrum includes the step of applying a transform to said spectrum so as to provide a set of coefficients such that each said coefficient depends on the entirety of said spectrum, said set of features including at least some of said coefficients provided by said transform.

46. A method of examining an object by energy dispersive x-ray diffraction comprising the steps of obtaining a spectrum of X-rays diffracted by said object and extracting a plurality of features from said spectrum constituting a feature set, said step of extracting said features from said spectrum including the step of applying a transform to said spectrum so as to provide a set of coefficients such that each said coefficient depends on the entirety of said spectrum, said set of features including at least some of said coefficients provided by said transform.

47. A method as claimed in claim 46 wherein said transform is a homomorphic transform.

48. A method as claimed in claim 46 wherein said transform is a cepstrum transform yielding an ordered set of cepstral coefficients.

49. A method as claimed in claim 48 wherein the set of features includes the lowest-ordered cepstral coefficients.

50. A method as claimed in claim 47 wherein said set of features consists entirely of said cepstral coefficients.

51. A method as claimed in claim 46 further comprising the step of classifying the structure of the object based on said features in said feature set.

* * * * *

UNITED STATES PATENT AND TRADEMARK OFFICE
CERTIFICATE OF CORRECTION

PATENT NO. : 6,118,850            Page 1 of 2
DATED : September 12, 2000
INVENTOR(S) : Mayo et al.

It is certified that error appears in the above-identified patent and that said Letters Patent is hereby corrected as shown below:

Col. 1, lines 12, 13 and 14, delete --The present application is a continuation of U.S. patent application Ser. No. 09/031,376, filed Feb. 27, 1998.--

Col. 2, line 8, "The" should read --the--.

Col. 6, line 27, "9$a$" should read --9A--.

Col. 6, line 34, "9$a$" should read --9A--.

Col. 6, line 35, "10$b$" should read --10B--.

Col. 7, line 11, "an" should read --a--.

Col. 7, line 50, "Detectors" should read --Detector--.

Col. 9, line 36, "is" should read --are--.

Col. 12, line 8, "patterns" should read --pattern--.

Col. 12, line 12, after "degrees" insert --.--.

Col. 13, line 39, after "312" insert --.--.

Col. 16, line 33, "in" should read --is--.

Col. 16, line 65, "systems" should read --system--.

Col. 17, line 61, "remembers" should read --remember--.

Col. 18, line 1 "Backpropagation" should read --backpropagation--.

Col. 19, line 19, "provide" should read --provides--.

UNITED STATES PATENT AND TRADEMARK OFFICE
CERTIFICATE OF CORRECTION

PATENT NO. : 6,118,850
DATED : September 12, 2000
INVENTOR(S) : Mayo et al.

It is certified that error appears in the above-identified patent and that said Letters Patent is hereby corrected as shown below:

Col. 18, line 34, "yield" should read --yields--.

Col. 19, line 31, after "seen" insert --to--.

Col. 20, line 64, "do" should read --does--.

Col. 21, line 31, after "reduces" delete "to".

Col. 22, line 15, "countermeasure" should read --countermeasures--.

Col. 24, line 3, after "twenty" insert -- - --.

Col. 24, line 21, after "twenty" insert -- - --.

Col. 27, line 56, "30" should read --29--.

Col. 29, line 33, "contribute" should read --contributes--.

Signed and Sealed this

Seventeenth Day of April, 2001

Attest:

NICHOLAS P. GODICI

Attesting Officer        Acting Director of the United States Patent and Trademark Office